US012712063B2

(12) United States Patent
Srivastava et al.

(10) Patent No.: US 12,712,063 B2
(45) Date of Patent: Aug. 18, 2026

(54) SYSTEMS AND METHODS FOR TRIAGING PATIENTS

(71) Applicant: Boston Scientific Neuromodulation Corporation, Valencia, CA (US)

(72) Inventors: Kyle Harish Srivastava, Saint Paul, MN (US); Nina Pehler, Edina, MN (US); Diana-Lyn Catherine DeCarlo, Sacramento, CA (US); Rex James Woon, San Gabriel, CA (US); Dat Thanh Huynh, North Hollywood, CA (US); Amarpreet Singh Bains, Woodbury, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 41 days.

(21) Appl. No.: 18/381,338

(22) Filed: Oct. 18, 2023

(65) Prior Publication Data

US 2024/0127926 A1 Apr. 18, 2024

Related U.S. Application Data

(60) Provisional application No. 63/417,070, filed on Oct. 18, 2022, provisional application No. 63/417,081, filed on Oct. 18, 2022.

(51) Int. Cl.
*G16H 40/67* (2018.01)
*G16H 20/70* (2018.01)
*G16H 40/40* (2018.01)

(52) U.S. Cl.
CPC ............ *G16H 20/70* (2018.01); *G16H 40/40* (2018.01); *G16H 40/67* (2018.01)

(58) Field of Classification Search
None
See application file for complete search history.

(56) References Cited

U.S. PATENT DOCUMENTS 4,620,543 A * 11/1986 Heppenstall ....... A61N 1/36034 607/51
7,676,272 B2 3/2010 Lang
(Continued)

FOREIGN PATENT DOCUMENTS

WO WO-2024086204 A1 4/2024
WO WO-2024086537 A1 4/2024

OTHER PUBLICATIONS

"International Application Serial No. PCT/US2023/035380, International Preliminary Report on Patentability mailed May 1, 2025", 10 pgs.

(Continued)

*Primary Examiner* — John A Pauls
(74) *Attorney, Agent, or Firm* — Schwegman Lundberg & Woessner, P.A.

(57) ABSTRACT

A medical system may include a patient system configured to determine a condition of a patient and deliver a neuromodulation therapy. The patient system may include a patient device having a user interface configured to enable patient interaction by the patient with the patient system. The patient system may include a triage system configured to select a triage tier from two or more triage tiers available for selection and indicative of a priority ranking for patient intervention. The triage system may be configured to use both the interaction and the condition to select the triage tier.

20 Claims, 11 Drawing Sheets

(56) References Cited

U.S. PATENT DOCUMENTS

| | | | | |
|---|---|---|---|---|
| 7,904,166 | B2 | 3/2011 | Diebold et al. | |
| 8,306,624 | B2 | 11/2012 | Gerber et al. | |
| 8,369,937 | B2 | 2/2013 | Bardy | |
| 8,438,039 | B2 | 5/2013 | Gottesman et al. | |
| 8,527,059 | B2 | 9/2013 | Demulling et al. | |
| 8,983,616 | B2 | 3/2015 | Kaula et al. | |
| 9,067,076 | B2 | 6/2015 | Nolan et al. | |
| 9,533,161 | B2 | 1/2017 | Matos | |
| 9,848,058 | B2 | 12/2017 | Johnson et al. | |
| 10,055,550 | B2 | 8/2018 | Goetz | |
| 10,315,038 | B2 | 6/2019 | Suryavanshi | |
| 10,493,282 | B2 | 12/2019 | Caparso et al. | |
| 10,843,001 | B2 | 11/2020 | Parker | |
| 11,296,971 | B1 * | 4/2022 | Jain | H04L 41/22 |
| 2003/0176785 | A1 * | 9/2003 | Buckman | A61B 5/117 600/431 |
| 2005/0075669 | A1 * | 4/2005 | King | A61N 1/36021 424/9.2 |
| 2005/0107846 | A1 | 5/2005 | Sweeney | |
| 2010/0211135 | A1 | 8/2010 | Caparso et al. | |
| 2014/0207486 | A1 * | 7/2014 | Carty | G16H 40/67 705/2 |
| 2014/0277253 | A1 * | 9/2014 | Jaax | A61N 1/36514 607/44 |
| 2016/0162656 | A1 * | 6/2016 | Di Lascia | G16H 20/10 705/2 |
| 2017/0095217 | A1 * | 4/2017 | Hubert | A61B 5/742 |
| 2020/0147393 | A1 | 5/2020 | Zhang et al. | |
| 2020/0353264 | A1 | 11/2020 | Gillespie et al. | |
| 2021/0196956 | A1 | 7/2021 | Juárez Paz | |
| 2021/0383922 | A1 | 12/2021 | Horton et al. | |
| 2022/0028566 | A1 | 1/2022 | Debates et al. | |
| 2022/0230742 | A1 | 7/2022 | Zenisek et al. | |
| 2022/0230743 | A1 | 7/2022 | Zenisek et al. | |
| 2024/0127927 | A1 | 4/2024 | Srivastava et al. | |

OTHER PUBLICATIONS

"International Application Serial No. PCT/US2023/035380, International Search Report mailed Mar. 28, 2024", 5 pgs.

"International Application Serial No. PCT/US2023/035380, Invitation to Pay Additional Fees mailed Feb. 7, 2024", 11 pgs.

"International Application Serial No. PCT/US2023/035380, Written Opinion mailed Mar. 28, 2024", 8 pgs.

"U.S. Appl. No. 18/381,384, Non Final Office Action mailed Jul. 2, 2025", 19 pgs.

"U.S. Appl. No. 18/381,384, Response filed Oct. 2, 2025 to Non Final Office Action mailed Jul. 2, 2025", 12 pgs.

"U.S. Appl. No. 18/381,384, Examiner Interview Summary mailed Mar. 13, 2026", 2 pgs.

"U.S. Appl. No. 18/381,384, Final Office Action mailed Jan. 14, 2026", 21 pgs.

"U.S. Appl. No. 18/381,384, Response filed Mar. 16, 2026 to Final Office Action mailed Jan. 14, 2026", 18 pgs.

* cited by examiner

100
PATIENT SYSTEM
101
SENSOR(S)
102
NEUROMODULATOR
103
PATIENT DEVICE(S)
REMOTE CONTROL
104
WATCH
105
PHONE / TABLET
106

311
PROGRAMMING
DEVICE
308
USER
INTERFACE
302
MEDICAL DEVICE
(E.G., ELECTRICAL THERAPY
DEVICE SUCH AS
A NEUROMODULATION DEVICE)
313
ELECTRODES

414
EXTERNAL SYSTEM
404
411
415
AMBULATORY MEDICAL DEVICE
(E.G. IMPLANTABLE OR WEARABLE)
SCS EXAMPLE
DBS EXAMPLE

| | PATIENT CONDITION POOR | PATIENT CONDITION MEDIOCRE | PATIENT CONDITION GOOD |
|---|---|---|---|
| INTERACTION POOR | TIER 1 | TIER 3 | TIER 4 |
| INTERACTION GOOD | TIER 2 | TIER 3 | TIER 5 |

SYSTEMS AND METHODS FOR TRIAGING PATIENTS

CLAIM OF PRIORITY

This application claims the benefit of U.S. Provisional Application No. 63/417,070, filed on Oct. 18, 2022 and U.S. Provisional Application No. 63/417,081, filed on Oct. 18, 2022, which are hereby incorporated by reference in their entireties.

TECHNICAL FIELD

This document relates generally to medical systems, and more particularly, but not by way of limitation, to systems, devices, and methods for using collected healthcare-related data to improve patient satisfaction with their medical system.

BACKGROUND

Healthcare relates to the preservation of health (e.g., preservation of mental and/or physical) by preventing, treating or managing illness. A trend in healthcare is to collect and analyze large amounts of data, referred to herein as "healthcare-related data" as it is data useful for providing or analyzing healthcare. For example, remote patient monitoring may be used to provide large amounts of healthcare-related data at the fingertips of both patients and healthcare providers.

Some systems are configured solely as a data collection system for purpose of collecting and transferring data. Other systems combine data collection with a therapy. For example, a system may include a data collection platform, The term "data collection platform" generally refers to technology (e.g., a combination of hardware, firmware and software) that provides a set of capabilities for collecting data that can be used by the system. A data collection platform may be a single data collection platform or may be organized as more than one data collection platform that are configured to cooperate with each other. A data collection platform may be on one device or may be distributed among more than one device in the system, including a therapy device(s). Thus, for example, a therapy device such as an implanted neuromodulator may provide some of the collected data, and a user device with a user interface may provide other of the collected data. A data collection platform may include sensor(s) and other data source(s). A data collection platform may, among other functions, allow data to be collected and served to users or applications.

A system may also include at least one medical device that is configured to deliver a therapy such as an electrical or drug therapy. A non-limiting example of a medical device to deliver a drug therapy is an insulin pump, and non-limiting examples of a medical device configured to deliver electrical therapy muscle stimulators, cardiac rhythm devices such as pacemakers and defibrillators, and neurostimulators. Examples of neuromodulation include Spinal Cord Stimulation (SCS), Deep Brain Stimulation (DBS), Peripheral Nerve Stimulation (PNS), and Functional Electrical Stimulation (FES). Physiological signal(s) may be sensed for various reasons related to the delivered therapy, such as to time the therapy delivery, to determine enabling or disabling conditions for delivering the therapy, to determine an efficacy of a therapy, or to provide feedback for closed-loop control of the therapy. In some non-limiting examples, glucose readings from a continuous glucose monitor may be used to provide closed-loop control of an insulin pump, and action potentials within a nerve may be sensed to provide closed-loop control of a neuromodulation therapy. Such systems may also be configured to receive user inputted data, such as but not limited to diet, carb counts or exercise information for the insulin pump systems or pain-related data for a neuromodulation (e.g., spinal cord stimulation) therapy.

Remote patient monitoring platforms allow clinicians, device reps, and patient care to monitor large patient populations. However, it may be difficult and time consuming to go through every patient to determine if they need help. It is desired to improve the management and assistance provided to remotely managed patient populations.

SUMMARY

Various embodiments of the present subject matter separate patients into several tiers to triage the patient for intervention by a clinician or device rep (or other patient intervention via a phone call, text, an in-app message such as educational videos, setting appointments with clinicians, video calls, and the like) and/or provide patient assistance when it is determined that the patient may be experiencing a common issue that can adversely affect patient satisfaction with the system.

An example (e.g., Example 1) of a medical system may include a patient system configured to determine a condition of a patient and deliver a neuromodulation therapy. The patient system may include a patient device having a user interface configured to enable patient interaction by the patient with the patient system. The patient system may include a triage system configured to select a triage tier from two or more triage tiers available for selection and indicative of a priority ranking for patient intervention. The triage system may be configured to use both the interaction and the condition to select the triage tier.

In Example 2, the subject matter of Example 1 may optionally be configured such that the patient system includes a patient monitoring system configured to determine the condition of the patient, and a neuromodulation system configured to deliver a neuromodulation therapy, wherein the patient device is configured to interact with the neuromodulation system.

In Example 3, the subject matter of any one or more of Examples 1-2 may optionally be configured such that the triage system includes a remote system configured for use in providing the patient intervention to improve the condition of the patient. The patient intervention may include at least one of reprogramming, a phone call, or an in-app patient message.

In Example 4, the subject matter of any one or more of Examples 1-3 may optionally be configured such that the triage system is configured to use a classification of the condition of the patient and a classification of the patient interaction to select the triage tier.

In Example 5, the subject matter of Example 4 may optionally be configured such that the classification of the condition includes a good condition and a poor condition, the classification of the patient interaction includes a good interaction and a poor interaction, and the two or more triage tiers available for selection include at least four tiers. The tiers may include a first tier corresponding to the poor condition and the poor patient interaction, a second tier corresponding to the poor condition and the good patient interaction, a third tier corresponding to the good condition and the poor interaction, and a fourth tier corresponding to the good condition and the good patient interaction.

In Example 6, the subject matter of Example 5 may optionally be configured such that the classification of the condition includes a mediocre condition between the good condition and the poor condition, and the at least four tiers include a tier corresponding to the mediocre condition and the good patient interaction.

In Example 7, the subject matter of any one or more of Examples 1-6 may optionally be configured such that the condition for the patient is determined from at least one of a pain state, a satisfaction score, a pain score, or duration in pain state.

In Example 8, the subject matter of any one or more of Examples 1-7 may optionally be configured such that the condition for the patient is determined from at least one of a sleep score, a mood score, or an activity score.

In Example 9, the subject matter of any one or more of Examples 1-8 may optionally be configured such that the condition for the patient is determined from at least one sensed patient parameter.

In Example 10, the subject matter of any one or more of Examples 1-9 may optionally be configured such that the condition for the patient is determined from free text.

In Example 11, the subject matter of any one or more of Examples 1-10 may optionally be configured such that the condition for the patient is determined by receiving at least one of a remote control rating log, whether the patient would recommend the neurostimulation therapy to another person, or the use of a communication channel with medical device reps.

In Example 12, the subject matter of any one or more of Examples 1-11 may optionally be configured such that the condition for the patient is determined by tracking web portal activity for patients by a clinician or a rep, or determining factors other than the neurostimulation therapy that may be influencing a pain state.

In Example 13, the subject matter of any one or more of Examples 1-12 may optionally be configured such that the patient interaction for the patient is determined by determining how often the patient changes a parameter of the neurostimulation therapy.

In Example 14, the subject matter of any one or more of Examples 1-13 may optionally be configured such that the patient interaction for the patient is determined by determining how often the patient changes programs used to deliver the neurostimulation therapy.

In Example 15, the subject matter of any one or more of Examples 1-14 may optionally be configured such that the patient system is configured to enable the patient to toggle the neurostimulation therapy ON and OFF. The patient interaction may be determined by determining how long the patient has left the neurostimulation therapy OFF or how long the patient has left the neurostimulation therapy ON.

Example 16 includes subject matter (such as a method, means for performing acts, machine readable medium including instructions that when performed by a machine cause the machine to perform acts, or an apparatus to perform). The subject matter may include delivering a neuromodulation therapy to a patient to treat a condition of the patient, determining the condition of the patient, receiving interaction from the patient with a system configured to deliver the neuromodulation therapy, and using both the determined condition of the patient and the interaction from the patient to triage the patient into one of a set of two or more triage tiers indicative of a priority ranking for patient intervention.

In Example 17, the subject matter of Example 16 may optionally be configured to further include using a patient monitoring system configured to determine the condition of the patient, and using a neuromodulation system to deliver a neuromodulation therapy.

In Example 18, the subject matter of any one or more of Examples 16-17 may optionally be configured to further include using a remote system to provide the patient intervention to improve the condition of the patient, wherein the patient intervention includes at least one of reprogramming, a phone call, or an in-app patient message.

In Example 19, the subject matter of any one or more of Examples 16-18 may optionally be configured to include using a classification of the condition of the patient and a classification of the patient interaction to select the triage tier.

In Example 20, the subject matter of any one or more of Examples 16-19 may optionally be configured such that the classification of the condition includes a good condition and a poor condition, the classification of the patient interaction includes a good interaction and a poor interaction, and the two or more triage tiers available for selection include at least four tiers. The tiers may include a first tier corresponding to the poor condition and the poor patient interaction, a second tier corresponding to the poor condition and the good patient interaction, a third tier corresponding to the good condition and the poor interaction, and a fourth tier corresponding to the good condition and the good patient interaction.

In Example 21, the subject matter of Example 20 may optionally be configured such that the classification of the condition includes a mediocre condition between the good condition and the poor condition, and the at least four tiers include a tier corresponding to the mediocre condition and the good patient interaction.

In Example 22, the subject matter of any one or more of Examples 16-21 may optionally be configured to further include determining the patient condition by receiving, for the patient, at least one of at pain state, a satisfaction score, a pain score, or duration in pain state.

In Example 23, the subject matter of any one or more of Examples 16-22 may optionally be configured to further include determining the patient condition by receiving, for the patient, at least one of a sleep score, a mood score, or an activity score.

In Example 24, the subject matter of any one or more of Examples 16-23 may optionally be configured to further include determining the patient condition by receiving, for the patient, sensed patient parameters, and determining the patient condition from the sensed patient parameters.

In Example 25, the subject matter of any one or more of Examples 16-24 may optionally be configured to further include determining the patient condition by receiving, for the patient, free text, and determining the patient condition from the free text.

In Example 26, the subject matter of any one or more of Examples 16-25 may optionally be configured to further include determining the patient condition by receiving, for the patient, a remote control rating log, whether the patient would recommend the neurostimulation therapy to another person, or the use of a communication channel with medical device reps.

In Example 27, the subject matter of any one or more of Examples 16-26 may optionally be configured to further include determining the patient condition by tracking web portal activity for patients by a clinician or a rep, or determining factors other than the neurostimulation therapy that may be influencing a pain state.

In Example 28, the subject matter of any one or more of Examples 16-27 may optionally be configured to further include determining the patient interaction by determining how often the patient changes a parameter of the neurostimulation therapy.

In Example 29, the subject matter of any one or more of Examples 16-28 may optionally be configured to further include determining the patient interaction by determining how often the patient changes programs used to deliver the neurostimulation therapy.

In Example 30, the subject matter of any one or more of Examples 16-29 may optionally be configured to further include determining the patient interaction by determining how long the patient has left the neurostimulation therapy OFF or how long the patient has left the neurostimulation therapy ON.

Example 31 includes subject matter (such as a device, apparatus, or machine) that may include non-transitory machine-readable medium including instructions, which when executed by a machine, cause the machine to perform a method including delivering a neuromodulation therapy to a patient to treat a condition of the patient, determining the condition of the patient, receiving interaction from the patient with a system configured to deliver the neuromodulation therapy, and using both the determined condition of the patient and the interaction from the patient to triage the patient into one of a set of two or more triage tiers indicative of a priority ranking for patient intervention.

In Example 32, the subject matter of Example 31 may optionally be configured such that the method further includes using a patient monitoring system configured to determine the condition of the patient, and using a neuromodulation system to deliver a neuromodulation therapy.

In Example 33, the subject matter of any one or more of Examples 31-32 may optionally be configured such that the method further includes using a remote system to provide the patient intervention to improve the condition of the patient. The patient intervention may include at least one of reprogramming, a phone call, or an in-app patient message.

In Example 34, the subject matter of any one or more of Examples 31-33 may optionally be configured such that the method further includes using a classification of the condition of the patient and a classification of the patient interaction to select the triage tier.

In Example 35, the subject matter of any one or more of Examples 31-34 may optionally be configured such that the classification of the condition includes a good condition and a poor condition, the classification of the patient interaction includes a good interaction and a poor interaction, and the two or more triage tiers available for selection include at least four tiers. The tiers may include a first tier corresponding to the poor condition and the poor patient interaction, a second tier corresponding to the poor condition and the good patient interaction, a third tier corresponding to the good condition and the poor interaction, and a fourth tier corresponding to the good condition and the good patient interaction.

An example (e.g., Example 36) of a medical system may include a patient system configured for use to determine health-related information for a patient, and deliver a neuromodulation therapy. The patient system may include a patient device having a user interface, storage for storing patient assistance data for each of a plurality of issues that may adversely affect patient satisfaction with the patient system, and a satisfaction monitor configured to determine, from the health-related information, that at least one of the plurality of issues may be adversely affecting the patient satisfaction, and send the patient assistance data, that corresponds to the at least one of the plurality of issues, to the user interface.

In Example 37, the subject matter of Example 36 may optionally be configured such that the plurality of issues includes improper patient interaction with the patient system, and the satisfaction monitor is configured to determine, from the health-related information, that the patient may be improperly interacting with the patient system, and send educational material to the user interface for educating for educating the patient how to interact with the patient system.

In Example 38, the subject matter of Example 37 may optionally be configured such that the improper patient interaction includes improper use of the patient device, and the educational material includes a training video how to use the patient device.

In Example 39, the subject matter of any one or more of Examples 37-38 may optionally be configured such that the improper patient interaction includes improper charging of the patient device, and the educational material includes a training video how to recharge the patient device.

In Example 40, the subject matter of Example 39 may optionally be configured such that the health-related information used to determine the improper charging of the patient device includes: consistently low battery voltage; slow charging rates; insufficient maximum battery voltage; high thermistor values during charging; low charge current; device state timing, wherein the device state includes device ON, device OFF, or device hibernation; or topic modeling of free text to detect the improper charging within the free text.

In Example 41, the subject matter of any one or more of Examples 37-40 may optionally be configured such that the improper patient interaction includes a problem with changing neurostimulation programs, and the educational material includes a training video how to change the neurostimulation programs. The health-related information used to determine the problem with changing neurostimulation programs may include poor pain outcomes from the neural stimulation therapy and no neurostimulation programming changes, stimulator usage, program usage, or topic modeling of free text to detect the problems with changing neurostimulation programming changes within the free text.

In Example 42, the subject matter of any one or more of Examples 37-41 may optionally be configured such that the improper patient interaction includes a problem with changing or starting neurostimulation schedules. The health-related information used to determine the problem with changing or starting neurostimulation schedules may include poor pain outcomes from the neural stimulation therapy and scheduling not used.

In Example 43, the subject matter of any one or more of Examples 37-42 may optionally be configured such that the improper patient interaction may include a failed data upload, and the educational material may include a training video how to upload data. The health-related information used to determine the failed data upload may include a lack of uploaded data from the patient system, app logs showing failed data uploads, or topic modeling of free text to detect the failed data upload.

In Example 44, the subject matter of any one or more of Examples 37-43 may optionally be configured such that the improper patient interaction includes an improper connection or recharging of a watch, and the educational material includes a training video how to connect and/or recharge the watch to an app on the patient device. The health-related information used to determine the problem with improper connection or recharging of the watch may include a lack of uploaded watch data, consistently low watch battery levels, or topic modeling of free text to detect the problem with improper connection or recharging of the watch.

In Example 45, the subject matter of any one or more of Examples 46-44 may optionally be configured such that the plurality of issues includes stimulation that is either ineffective or has adverse side effects. The satisfaction monitor may be configured to determine, from the health-related information, that the stimulation is ineffective or has adverse side effects, and to send troubleshooting recommendations for the patient to troubleshoot the stimulation.

In Example 46, the subject matter of Example 45 may optionally be configured such that the satisfaction monitor is further configured to alert the clinician rep that the patient should be reprogrammed if the troubleshooting is not successful in providing efficacious stimulation without the adverse side effects.

In Example 47, the subject matter of any one or more of Examples 45-46 may optionally be configured such that the health-related information used to determine that the stimulation is ineffective or has adverse side effects includes topic modeling of free text to detect that the stimulation is ineffective or has adverse side effects.

In Example 48, the subject matter of Example 47 may optionally be configured such that the satisfaction monitor is configured to send a campaign to the patient device to have the patient determine overlap between stimulation and pain area, and suggest a program change or alert a rep that the patient needs reprogramming if the stimulation does not adequately overlap the pain area.

In Example 49, the subject matter of Example 47 may optionally be configured such that the satisfaction monitor is configured to send a campaign to the patient device to have the patient measure at least one impedance of the device, compare the measured at least one impedance to a threshold, and alert a rep that the patient needs reprogramming when the measured at least one impedance exceeds the threshold.

In Example 50, the subject matter of Example 47 may optionally be configured such that the satisfaction monitor is configured to determine if the patient considers the stimulation to be too strong or too weak, to suggest amplitude changes if the patient considers the stimulation to be too strong or too weak, and to alert a rep that the patient needs reprogramming if the amplitude changes do not remedy the stimulation that is too strong or too weak.

Example 51 includes subject matter (such as a method, means for performing acts, machine readable medium including instructions that when performed by a machine cause the machine to perform acts, or an apparatus to perform). The subject matter may be performed using a medical system that includes a patient system configured to determine health-related information for a patient and deliver a neuromodulation therapy. The subject matter may include using the patient system to determine health-related information for a patient and deliver neuromodulation therapy to the patient, identifying, from the health-related information, at least one of a plurality of issues that may be adversely affecting patient satisfaction for the patient system, wherein the plurality of issues corresponds to stored patient assistance data, and sending the patient assistance data, that corresponds to the at least one of the plurality of issues, to a user interface of a patient device within the patient system.

In Example 52, the subject matter of Example 51 may optionally be configured such that the plurality of issues includes improper patient interaction with the patient system, and the educational material includes educational material for educating the patient how to interact with the patient system.

In Example 53, the subject matter of Example 52 may optionally be configured such that the improper patient interaction includes improper use of the patient device, and the educational material includes a training video how to use the patient device.

In Example 54, the subject matter of any one or more of Examples 51-53 may optionally be configured such that the improper patient interaction includes improper charging of the patient device, and the educational material includes a training video how to recharge the patient device.

In Example 55, the subject matter of Example 54 may optionally be configured such that the health-related information used to identify the improper charging of the patient device includes: consistently low battery voltage; slow charging rates; insufficient maximum battery voltage; high thermistor values during charging; low charge current; device state timing, wherein the device state includes device ON, device OFF, or device hibernation; or topic modeling of free text to detect the improper charging within the free text.

In Example 56, the subject matter of any one or more of Examples 51-55 may optionally be configured such that the improper patient interaction includes a problem with changing neurostimulation programs. The educational material may include a training video how to change the neurostimulation programs. The health-related information used to identify the problem with changing neurostimulation programs includes: poor pain outcomes from the neural stimulation therapy and no neurostimulation programming changes; stimulator usage; program usage; or topic modeling of free text to detect the problems with changing neurostimulation programming changes within the free text.

In Example 57, the subject matter of any one or more of Examples 51-56 may optionally be configured such that the improper patient interaction includes a problem with changing or starting neurostimulation schedules, and the health-related information used to identify the problem with changing or starting neurostimulation schedules includes poor pain outcomes from the neural stimulation therapy and scheduling not used.

In Example 58, the subject matter of any one or more of Examples 51-57 may optionally be configured such that the improper patient interaction includes a failed data upload, the educational material includes a training video how to upload data, and the health-related information used to identify the failed data upload includes a lack of uploaded data from the patient system, app logs showing failed data uploads, or topic modeling of free text to detect the failed data upload.

In Example 59, the subject matter of any one or more of Examples 51-58 may optionally be configured such that the improper patient interaction includes an improper connection or recharging of a watch, the educational material includes a training video how to connect and/or recharge the watch to an app on the patient device, and the health-related information used to identify the problem with improper connection or recharging of the watch includes a lack of uploaded watch data, consistently low watch battery levels, or topic modeling of free text to detect the problem with improper connection or recharging of the watch.

In Example 60, the subject matter of any one or more of Examples 51-59 may optionally be configured such that the plurality of issues includes stimulation that is either ineffective or has adverse side effects, and the method includes sending troubleshooting recommendations for the patient to troubleshoot the stimulation when the stimulation is determined to be ineffective or to have adverse side effects.

In Example 61, the subject matter of Example 60 may optionally be configured to further include alerting a clinician or rep that the neuromodulation therapy should be reprogrammed if the troubleshooting is not successful in providing efficacious stimulation without the adverse side effects.

In Example 62, the subject matter of any one or more of Examples 60-61 may optionally be configured such that the health-related information used to determine that the stimulation is ineffective or has adverse side effects includes topic modeling of free text to detect that the stimulation is ineffective or has adverse side effects.

In Example 63, the subject matter of any one or more of Examples 60-62 may optionally be configured to further include sending a campaign to the patient device to have the patient determine overlap between stimulation and pain area, and suggesting a program change or alert a clinician or a rep that the neuromodulation therapy should be reprogrammed if the stimulation does not adequately overlap the pain area.

In Example 64, the subject matter of any one or more of Examples 51-63 may optionally be configured to further include sending a campaign to the patient device to have the patient measure at least one impedance of the device, comparing the measured at least one impedance to a threshold, and alerting a clinician or a rep that the neuromodulation therapy should be reprogrammed when the measured at least one impedance exceeds the threshold.

In Example 65, the subject matter of any one or more of Examples 51-64 may optionally be configured to further include determining if the patient considers the stimulation to be too strong or too weak, suggesting amplitude changes if the patient considers the stimulation to be too strong or too week, and alerting a clinician or a rep that the neuromodulation therapy should be reprogrammed if the amplitude changes do not remedy the stimulation that is too strong or too weak.

Example 66 includes subject matter (such as a device, apparatus, or machine) that may include non-transitory machine-readable medium including instructions, which when executed by a machine, cause the machine to perform a method including acquiring health-related information from a patient system that is configured to determine the health-related information for a patient and deliver a neurostimulation therapy, identifying, from the health-related information, at least one of a plurality of issues may be adversely affecting the patient satisfaction with the patient system, wherein the plurality of issues corresponds to stored patient assistance data, and sending the patient assistance data, that corresponds to the at least one of the plurality of issues, to a user interface of the patient system.

In Example 67, the subject matter of Example 66 may optionally be configured such that the at least one of the plurality of issues includes improper use of the patient device, and the patient assistance data includes a training video how to use the patient device.

In Example 68, the subject matter of any one or more of Examples 66-67 may optionally be configured such that the at least one of the plurality of issues includes improper charging of the patient device, and the patient assistance data includes a training video how to recharge the patient device.

In Example 69, the subject matter of any one or more of Examples 66-68 may optionally be configured such that the at least one of the plurality of issues includes a failed data upload, the patient assistance data includes a training video how to upload data, and the health-related information used to identify the failed data upload include a lack of uploaded data from the patient system, app logs showing failed data uploads, or topic modeling of free text to detect the failed data upload.

In Example 70, the subject matter of any one or more of Examples 66-69 may optionally be configured such that the at least one of the plurality of issues includes an improper connection or recharging of a watch, and the patient assistance data includes a training video how to connect and/or recharge the watch to an app on the patient device.

Any of Examples 1-15 may be combined with any of Examples 36-50. Any of Examples 16-30 may be combined with any of Examples 51-65. Any of Examples 31-35 may be combined with any of Examples 66-70.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figures 1, 2:
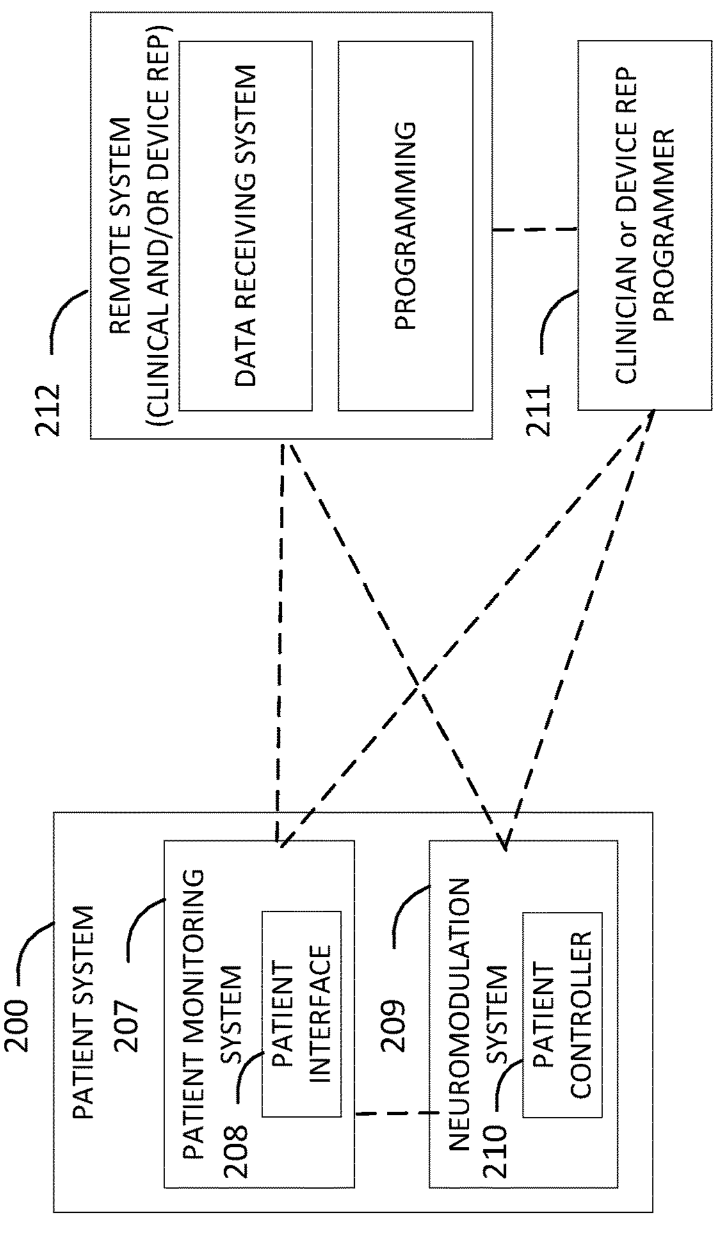
FIG. 1 illustrates, by way of example and not limitation, a patient system, and examples of devices that may make up components of the patient system
FIG. 2 illustrates, by way of example and not limitation, a medical system that includes a patient system, a remote system and a programmer.

FIG. 1 illustrates, by way of example and not limitation, a patient system, and examples of devices that may make up components of the patient system. The patient system 100 may include component(s) that act on the patient such as deliver a therapy to the patient, component(s) used to sense a condition, status or environment of the patient, and component(s) enabling the patient to interface with the patient system. For example, the illustrated patient system 100 may include sensor(s) 101 to sense patient parameter(s). Examples of sensors may include, but not limited to, neural activity, muscle movement, patient activity, patient posture, patient location, breathing, heart rate, blood pressure, temperature, analyte sensors and the like. The illustrated patient system 100 may include a therapy-delivering device such a neuromodulator 102 configured to deliver a neuromodulation therapy such as a DBS, SCS, PNS, FES, or TENS therapy. Those of ordinary skill in the art would understand, upon reading and comprehending the present disclosure, how to apply the present subject matter to other therapies, such as but not limited to cardiac rhythm therapies or drug pump therapies. The illustrated patient system 100 may also include device(s) 103 used by the patient to interface with the patient system. These device(s) may include sensor(s) (e.g., accelerometer, temperature sensor, heart rate sensor, etc.) and/or may be used to receive patient feedback such as responses to questions or free text responses. These device (s) may include interfaces used to interact with the therapy delivery. Examples of patient device(s) 103 include, but are not limited to, a patient remote control 104, a wearable device(s) such as a watch 105, or a phone or tablet 106, or another personal device.

FIG. 2 illustrates, by way of example and not limitation, a medical system that includes a patient system, a remote system and a programmer. The patient system 200 is illustrated to include a patient monitoring system 207 with a patient interface 208, and a neuromodulation system 209 with a patient controller 210. The functions performed by the patient monitoring system 207 may be performed using one device or may be distributed over more than one device. For example, a patient phone or watch may be an example of a one device that performs patient monitoring functions. A combination of sensors along with a phone or tablet may be an example of more than one device that work together to perform patent monitoring functions. Similarly, the functions performed by the neuromodulation system 209 may be performed by one device or may be distributed over more than one device. For example, an implantable neurostimulator may perform the neuromodulation functions. A combination of a remote control and at least one neurostimulator may perform a combination of neuromodulation functions (e.g., adjusting neuromodulation therapy programs or schedules, and providing the neuromodulation therapy). By way of another example, a neuromodulation system may use sensor(s) to enable/disable therapy or provide a closed loop therapy. Furthermore, one device may perform both functions of the patient monitoring system and function of the neuromodulation system. For example, a remote control or phone may be used to control the neuromodulation therapy and also provide questionnaires or free text capabilities which may be used to provide patient monitoring functions. By way of another example, a neuromodulator may provide the neuromodulation therapy, but may also include sensors for sensing patient parameters (e.g., accelerometer, electrical signal sensors, impedance sensors, and the like). A clinician or device rep programmer 211 may communicate with the patient system 200, such as for the purpose to program the system and/or receive patient health-related data. A remote system 212 may communicate with the programmer 211 and/or the patient system 200, such as for the purpose to program the system and/or receive patient health-related information.

Figures 3, 4:
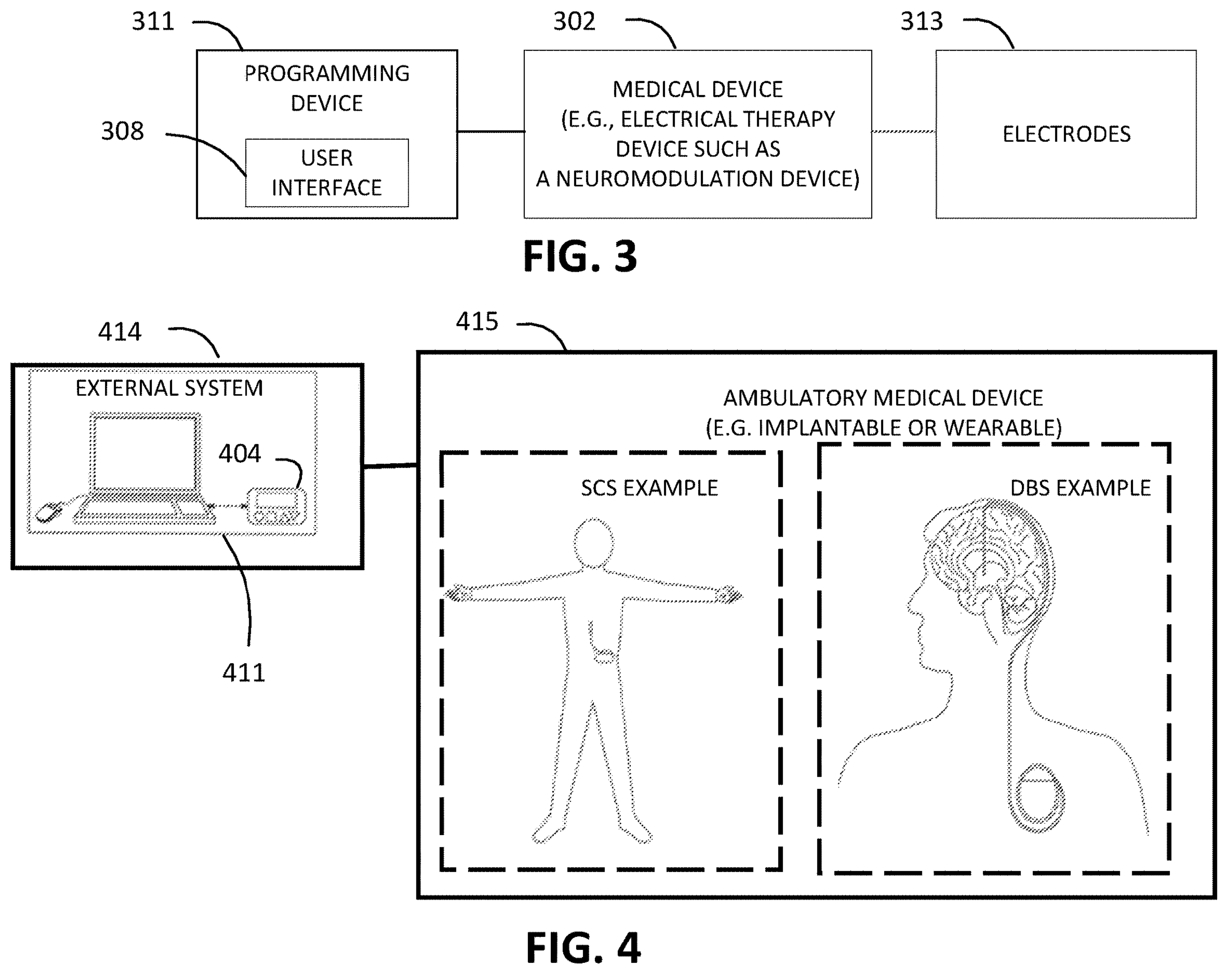
FIG. 3 illustrates a neuromodulation system as an example of a medical device system.
FIG. 4 illustrates, by way of example and not limitation, the neuromodulation system of FIG. 3 implemented in a spinal cord stimulation (SCS) system or a deep brain stimulation (DBS) system.

FIG. 3 illustrates a neuromodulation system as an example of a medical device system. The medical device 302 may be configured to deliver a therapy such as, by way of example and not limitation, an electrical therapy using electrodes 313. In the illustrated embodiment, the medical device may be a neuromodulation device, and the system may be a neuromodulation system 325. The system may include electrodes 313, the neuromodulation device 302 and a programming system such as a programming device 311. The programming system may include multiple devices. The electrodes 313 are configured to be placed on or near one or more neural targets in a patient. The neuromodulation device 302 is configured to be electrically connected to electrodes 313 and deliver neuromodulation energy, such as in the form of electrical pulses, to the one or more neural targets though electrodes 313. The system may also include sensing circuitry to sense a physiological signal, which may but does not necessarily form a part of neuromodulation device 302. The delivery of the neuromodulation is controlled using a plurality of modulation parameters that may specify the electrical waveform (e.g., pulses or pulse patterns or other waveform shapes) and a selection of electrodes through which the electrical waveform is delivered. In various embodiments, at least some parameters of the plurality of modulation parameters are programmable by a user, such as a physician, device rep, or other caregiver. The programming device 311 provides the user with accessibility to the user-programmable parameters. The programming device 311 may also provide the use with data indicative of the sensed physiological signal or feature(s) of the sensed physiological signal. In various embodiments, the programming device 311 is configured to be communicatively coupled to modulation device via a wired or wireless link. In various embodiments, the programming device 311 includes a user interface 308 such as a graphical user interface (GUI) that allows the user to set and/or adjust values of the user-programmable modulation parameters. The user interface 308 may also allow the user to view the data indicative of the sensed physiological signal or feature(s) of the sensed physiological signal and may allow the user to interact with that data. The data collection platform may be on one device or may be distributed among more than one device in the system. Thus, for example, the medical device 302 and programming device 311 may contribute to the collected data. The user interface 308 may be used to allow the user to answer questions to provide healthcare-related data. The electrode selection and other therapy parameters may also provide healthcare-related data. Additional sensor(s) may also provide healthcare-related data.

FIG. 4 illustrates, by way of example and not limitation, the neuromodulation system of FIG. 3 implemented in a spinal cord stimulation (SCS) system or a deep brain stimulation (DBS) system. The illustrated neuromodulation system includes an external system 414 that may include at least one programming device. The illustrated external system 414 may include a programmer 411 configured for use by a clinician or device rep to communicate with and program the neuromodulator, and a remote control 404 configured for use by the patient to communicate with and program the neuromodulator. For example, the remote control device may allow the patient to turn a therapy on and off and/or may allow the patient to adjust patient-programmable parameter (s) of the plurality of modulation parameters. FIG. 4 illustrates a medical device as an ambulatory medical device 415. Examples of ambulatory devices include wearable or implantable neuromodulators. The external system 414 may include a network of computers, including computer(s) remotely located from the ambulatory medical device 415 that are capable of communicating via one or more communication networks with the programmer 411 and/or the remote control 404. The remotely located computer(s) and the ambulatory medical device 415 may be configured to communicate with each other via another external device such as the programmer 411 or the remote control 404. The remote control device 404 and/or the programmer 411 may allow a user (e.g., patient and/or clinician or device rep) to answer questions as part of the data collection process. The ambulatory medical device may include internal or external sensors that may be used to collect data, which may form at least part of the healthcare-related data to be transferred to a data receiving system. Parameter data for the programmed therapy may form at least part of the healthcare-related data to be transferred to a data receiving system.

Figures 5, 6:
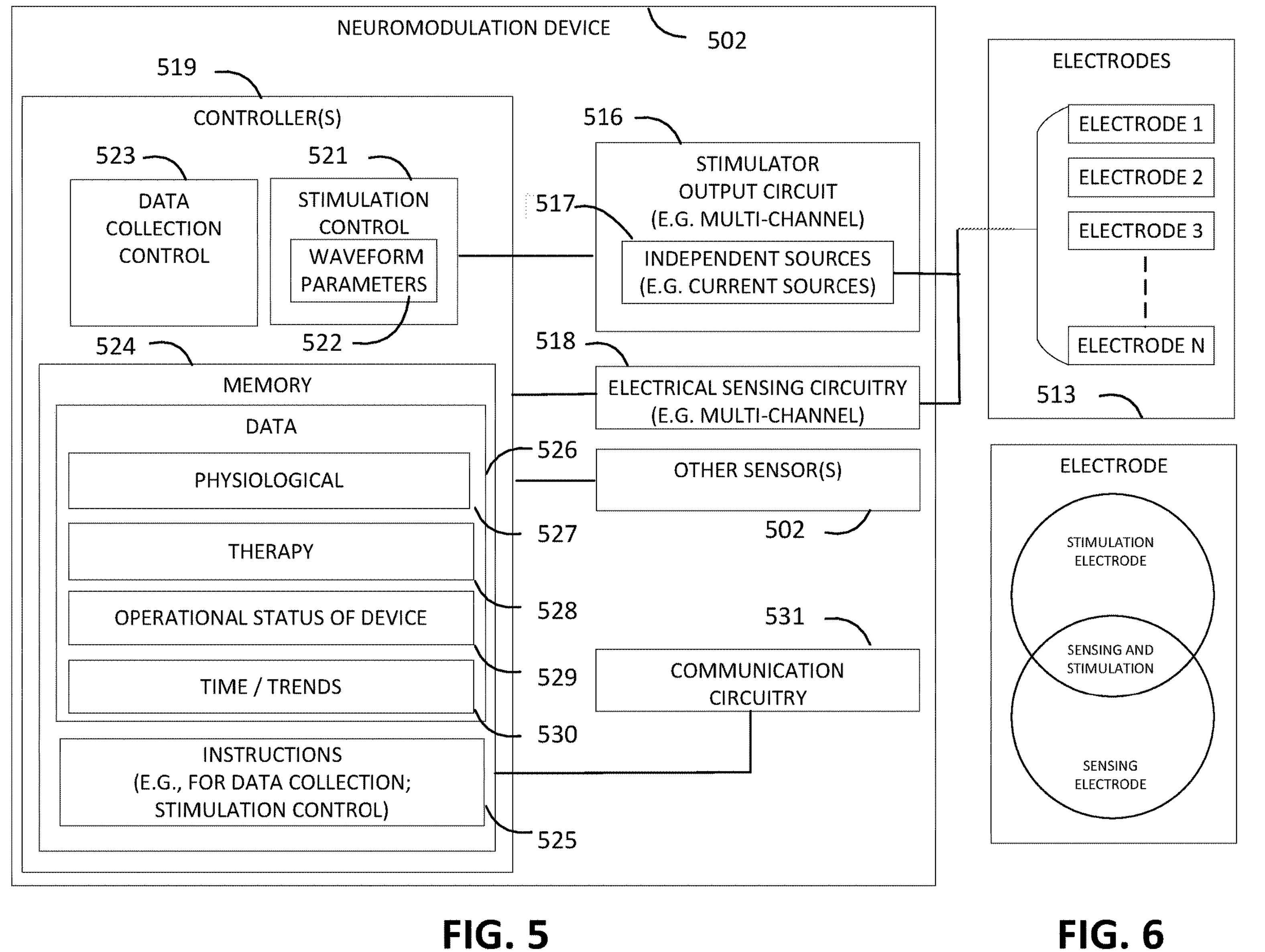
FIG. 5 illustrates, by way of example and not limitation, an embodiment of a neuromodulation device, such as may be implemented as the medical device illustrated in FIGS. 3 and 4.
FIG. 6 is a diagram illustrating, by way of example and not limitation, a relationship between a stimulation electrode and a sensing electrode.

FIG. 5 illustrates, by way of example and not limitation, an embodiment of a neuromodulation device, such as may be implemented as the medical device illustrated in FIGS. 3 and 4. The modulation device 502 may be configured to be connected to electrode(s) 513, illustrated as N electrodes. Any one or more of the electrodes 513 may be configured for use to deliver modulation energy, sense electrical activity, or both deliver modulation energy and sense electrical activity. The modulation device 502 may include a stimulator output circuit 516 configured to deliver modulation energy to electrode(s). The stimulator output circuit 516 may be configured with multiple (e.g., two or more) channels for delivering modulation energy, where each channel may be independently controlled with respect to other channel(s). For example, the stimulator output circuit 516 may have independent sources 517 such as independent current sources or independent voltage sources. The modulation device 502 may include electrical sensing circuitry 518 configured to receive sensed electrical energy from the electrode(s), such as may be used to sense electrical activity in neural tissue or muscle tissue. The sensing circuitry may be configured to process signals in multiple (e.g., two or more) channels. By way of example and not limitation, the electrical sensing circuitry 518 may be configured to amplify and filter the signal(s) in the channel(s). The controller 519 may be configured to detect one or more features in the sensed signals. Examples of features that may be detected include peaks (e.g., minimum and/or maximum peaks including local peaks/inflections), range between minimum/maximum peaks, local minima and/or local maxima, area under the curve (AUC), curve length between points in the curve, oscillation frequency, rate of decay after a peak, a difference between features, and a feature change with respect to a baseline. Detected feature(s) may be fed into a control algorithm, which may use relationship(s) between the feature(s) and waveform parameter(s) to determine feedback for closed-loop control of the therapy. Some embodiments of the modulation device 502 may include or be configured to receive data from other sensor(s) 520. The other sensor(s) 502 may include physiological sensor(s), environmental sensor(s), or proximity sensor(s). The modulation device 502 may include a controller 519 operably connected to the stimulation output circuit 516 and the sensing circuitry 518, 520. The controller 519 may include a stimulation control 521 configured for controlling the stimulator output circuit 516. For example, the stimulation control 521 may include start/stop information for the stimulation and/or may include relative timing information between stimulation channels. The stimulation control 521 may include waveform parameters 522 that control the waveform characteristics of the waveform produced by the stimulation output circuit 516. The waveform parameters 522 may include, by way of example and not limitation, amplitude, frequency, and pulse width parameters. The waveform parameters 522 may include, by way of example and not limitation, regular patterns such as patterns regularly repeat with same pulse-to-pulse interval and/or irregular patterns of pulses such as patterns with variable pulse-to-pulse intervals. The waveform parameters may, but do not necessary, define more than one waveform shape (e.g., including a shape other than square pulses with different widths or amplitudes). The stimulation control 521 may be configured to change waveform parameter(s) (e.g., one or more waveform parameters) in response to user input and/or automatically in response to feedback.

The controller 519 may include a data collection control 523 configured for use by the neuromodulation device 502 to collect healthcare related data. The controller 519 may include a memory 524 with instructions 525 for use to control the data collection and control the stimulation via the stimulation control 521. The memory 524 may also include storage for storing different types of collected healthcare-related data 526, such as physiological data 527, therapy data 528, data regarding the operational status of the device 529, and times/trends for data 530. Examples of physiological data 527 may include, by way of example and not limitation, heart rate, heart rate variability, oxygen saturation, activity, posture, steps, gait, temperature, evoked compound action potentials (ECAPS), electromyograms (EMGs), electroencephalograms (EEGs), weight, blood pressure, and the like. Examples of therapy data 528 may include, by way of example and not limitation, stimulations settings such as amplitude, pulse width, pulse frequency period, duration of burst of pulses, active electrodes, electrode fractionalization controlling the distribution of energy (e.g., current) to active electrodes, waveforms, pulse patterns including various complex patterns, and the like. Examples of data regarding the operational status of the device 529 may include, by way of example and not limitation, electrode-tissue impedance, fault conditions, battery information such as battery health, battery life, voltage, charge state, charging history if rechargeable, MRI status, Bluetooth connection logs, connection with Clinician Programmer, hours of operation/duration of implant, and the like. Other device information may include device model and lead model. Examples of time or trend data 530 may include changes (e.g., increases and/or decreases) in activity, pain, function and sleep. The neuromodulation device may include communication circuitry 531 configured for use to communicate with other device(s) such as a programmer, remote control, phone, tablet and the like. The healthcare-related data may be transferred out from the neuromodulation device for transfer to a data receiving system.

FIG. 6 is a diagram illustrating, by way of example and not limitation, a relationship between a stimulation electrode and a sensing electrode. The stimulation electrode is configured for use in delivering modulation energy, and the sensing electrode is configured for use in sensing electrical activity. As illustrated, the stimulation electrode may also be used in sensing electrical activity, and the sensing electrode may also be used in delivering modulation energy. Thus, the term "stimulation electrode" does not necessary exclude the electrode from also being used to sense electrical activity; and the term "sensing electrode" does not necessarily exclude the electrode from also being used to deliver modulation energy.

Figure 7:
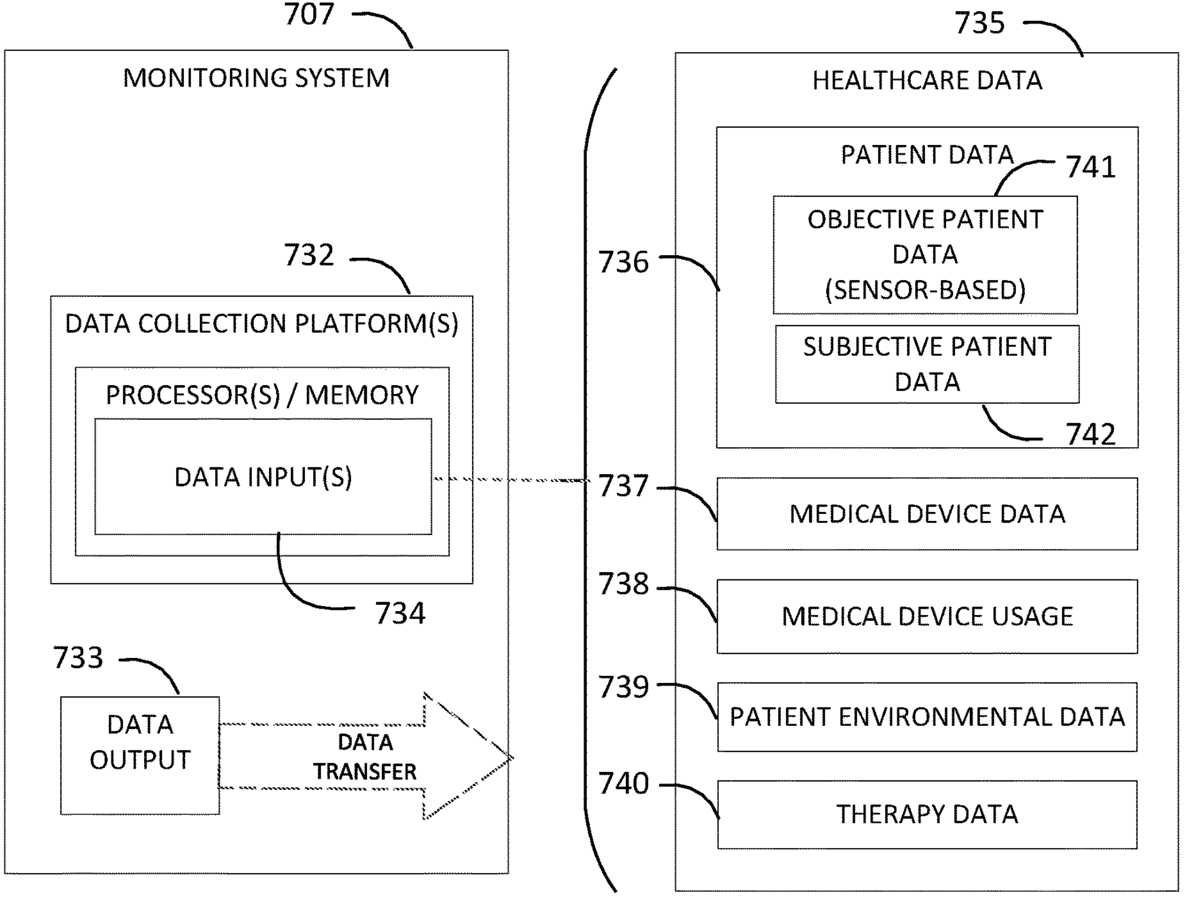
FIG. 7 illustrates, by way of example and not limitation, an embodiment of a monitoring system configured for use to collect healthcare-related data for transfer to a data receiving system.

FIG. 7 illustrates, by way of example and not limitation, an embodiment of a monitoring system configured for use to collect healthcare-related data for transfer to a data receiving system. The illustrated monitoring system 707 is configured to include at least one data collection platform 732 and a data output 733. The data collection platform(s) 732 is configured to collect healthcare-related data and the data output 733 is configured to transfer at least some of the collected data. The data collection platform(s) 732 may include at least one processor configured to execute instructions stored in memory (e.g., illustrated as processor(s)/memory) to enable data input(s) 734 for receiving or collecting healthcare data 735. Examples of healthcare data 735 may include patient data 736, medical device data 737, medical device usage 738, patient environmental data 739, therapy data 740, or various combinations thereof. The patient data 736 may include objective data 741 such as data collected from physiological sensor(s) and subjective data 742 such as data collected from user-answered question(s) (e.g., "How do you rate your pain?").

Figure 8:
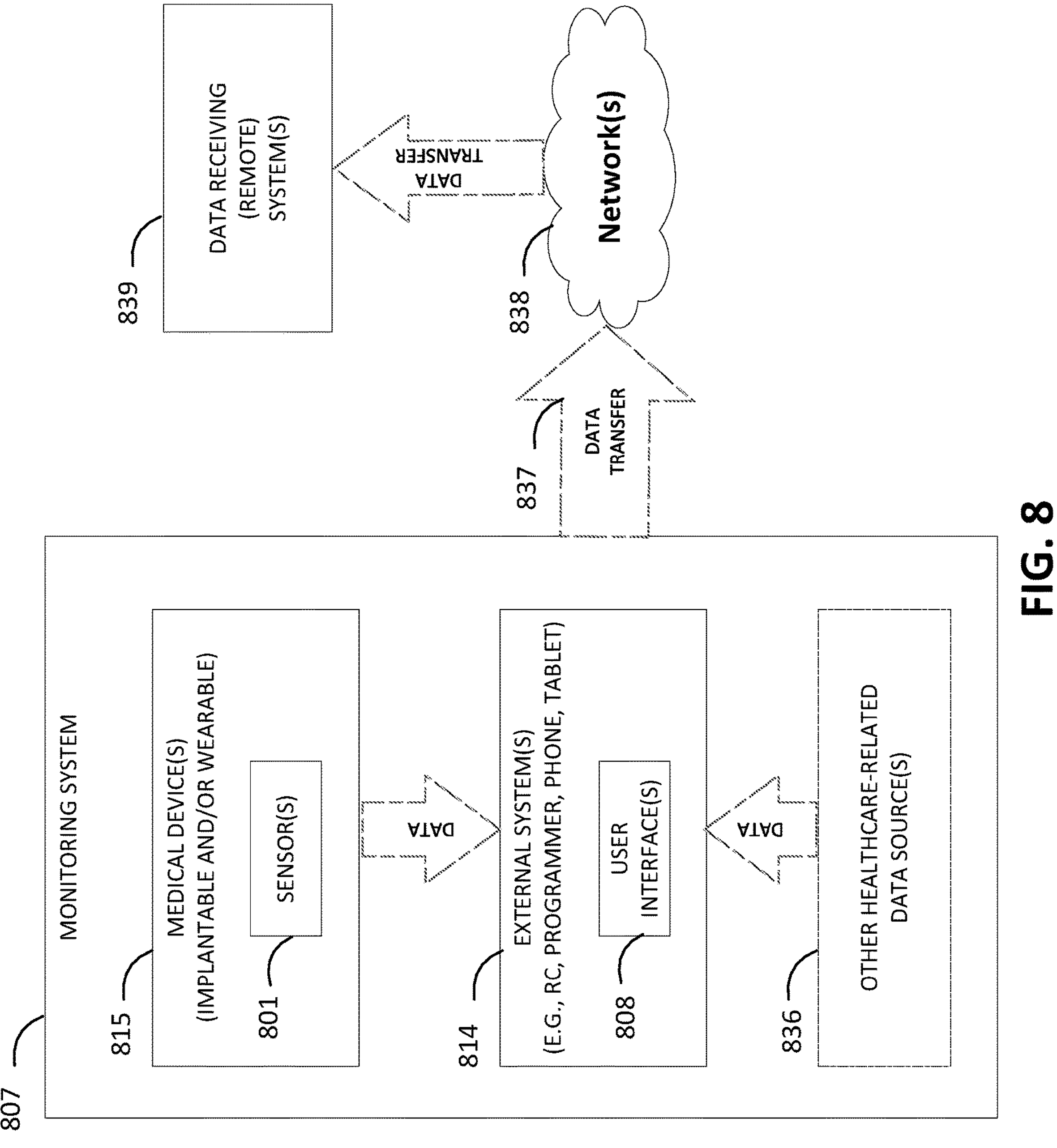
FIG. 8 illustrates, by way of example and not limitation, an embodiment of a monitoring system that may include medical device(s), external system(s) or other healthcare related data source(s) configured for use to collect healthcare-related data for transfer to a data receiving system.

FIG. 8 illustrates, by way of example and not limitation, an embodiment of a monitoring system that may include medical device(s), external system(s) or other healthcare related data source(s) configured for use to collect healthcare-related data for transfer to a data receiving system. One or more of the medical device(s) 815, external system(s) 814 or other healthcare-related data source(s) 836 may include technology used by the monitoring system 807 to collect data, and thus may form part of the data collection platform. The data collection platform may be on one device or may be distributed among more than one device in the system. The monitoring system 807 may include more than one medical device configured to communicate with each other or to an external system. Examples of medical devices 815 include implantable and wearable devices. The medical device may be configured to only collect data, to only deliver therapy, or to both collect data and deliver therapy. In the illustrated embodiment, the medical device includes sensor(s) 801 configured for use to collect patient data (e.g., objective patient data). The medical device may be configured to collect and provide medical device data such as device model, configuration, settings, and the like. Thus, the medical device may be configured to collect patient data, medical device data, medical device usage data, environmental data, and therapy data such as stimulation settings. Examples of external system(s) include remote controls, programmers, phones, tablets, smart watches, personal computers, and the like. In the illustrated embodiment, the external system(s) include at least one user interface 808 configured for use to receive user input, which may include user answers to questions. The user answers received via the user interface(s) 221 may include subjective patient data (e.g., "How do you rate your pain?" or "Where do you feel pain?") or objective patient data (e.g., "What is your heart rate?", "What is your blood pressure?", or "When did you fall asleep and wake up?"). The external system may be configured to collect medical device data from the medical device. The external system may be configured to collect environmental data or therapy data.

Other healthcare-related data source(s) 836 may include patient data received via a provider's server that stores patient health records. For example, patients may use a patient portal to access their health records such as test results, doctor notes, prescriptions, and the like. Other healthcare-related data sources may include various apps on a patient's phone or other device, or the data on a server accessed by those apps. By way of example and not limitation, this type of data may include heart rate, blood pressure, weight, and the like collected by the patient in their home, may include glucose measurements from a continuous glucose monitor. In another example, an app on a phone or patient's device may include or may be configured to access environmental data such as weather data and air quality information or location elevation data such as may be determined using cellular networks and/or a global positioning system (GPS). Weather data may include, but is not limited to, barometric pressure, temperature, sunny or cloud cover, wind speed, and the like.

The monitoring system 807 is configured to transfer data 837 via at least one network 838. The data transfer may use various network protocols to communicate and transfer data through one or more networks which may but does not necessarily include the Internet and/or various wireless networks, which may include short range wireless technology such as Bluetooth. The data may be transferred directly from at least one of the external systems and/or may be transferred directly from at least one of the medical device (s). As illustrated, the external system(s) 814 may be configured to receive data from the medical device(s) and/or receive data from other healthcare-related data source(s), and then transfer the data through the network(s) 838 to the data receiving system(s) 839.

Various embodiments of the present subject matter use monitored health-related information to improve the management and assistance provided to remotely managed patient populations, and thus improve a patient's experience with the patient system. For example, a patient may be receiving therapy, such as but not limited to a neuromodulation therapy, from one or more medical devices. By way of a specific example, the neuromodulation therapy may be an implantable neuromodulator configured to deliver a spinal cord stimulation (SCS) therapy or a deep brain stimulation (DBS) therapy. Some of these patients may benefit from assistance to improve the efficacy of their therapy or otherwise improve their experience with the system. For example, a patient may request assistance from a clinician or device rep regarding how to interact the medical device or to adjust the therapy provided by their device. To address this need, various embodiments of the present subject matter provide systems and methods to separate patients into several tiers to triage the patient for intervention by a clinician or device rep (or other patient intervention via a phone call, text, an in-app message such as educational videos, setting appointments with clinicians, video calls, and the like), and/or provide systems and methods for automatically providing patient assistance when it is automatically determined that the patient may be experiencing a common issue that can adversely affect patient satisfaction with the system. These embodiments may be implemented together to determine when and how to intervene with individual patients within the patient population such that the intervention (whether automatic assistance or assistance from a device rep or clinician) will likely quickly improve the overall patient satisfaction with the system for more of the patients in the patient population.

Triaging Patients

Various embodiments use patient monitoring to automatically triage patients, including escalating the patients in need of immediate intervention, with the most chance for success, to the top. More particularly, both patient condition and patient interaction with the system may be assessed to triage the patient.

Figure 9:
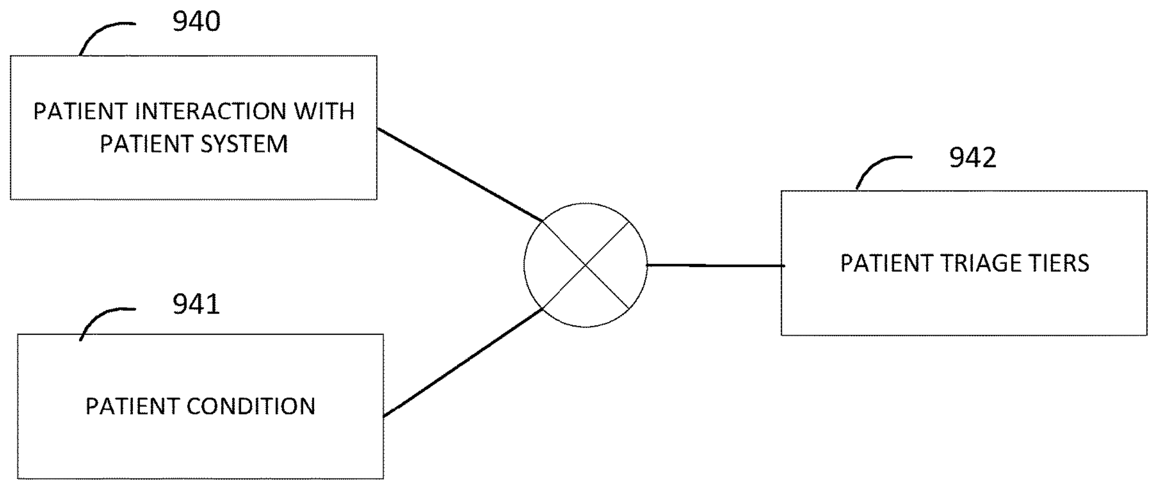
FIG. 9 illustrates, by way of example and not limitation, a process for triaging patients.

FIG. 9 illustrates, by way of example and not limitation, a process for triaging patients. The illustrated process uses indicators for both a patient interaction with a patient system 940 and a patient condition 941 as inputs for determining patient triage tiers 942. Thus, a patient may be given a higher priority if patient assistance such as educational material describing how to interact with the system or if reprogramming can make a big difference in the efficacy of the therapy. Conversely, a patient may be given a lower priority if the patient therapy is already efficacious and/or already is interacting with the system.

Figure 10:
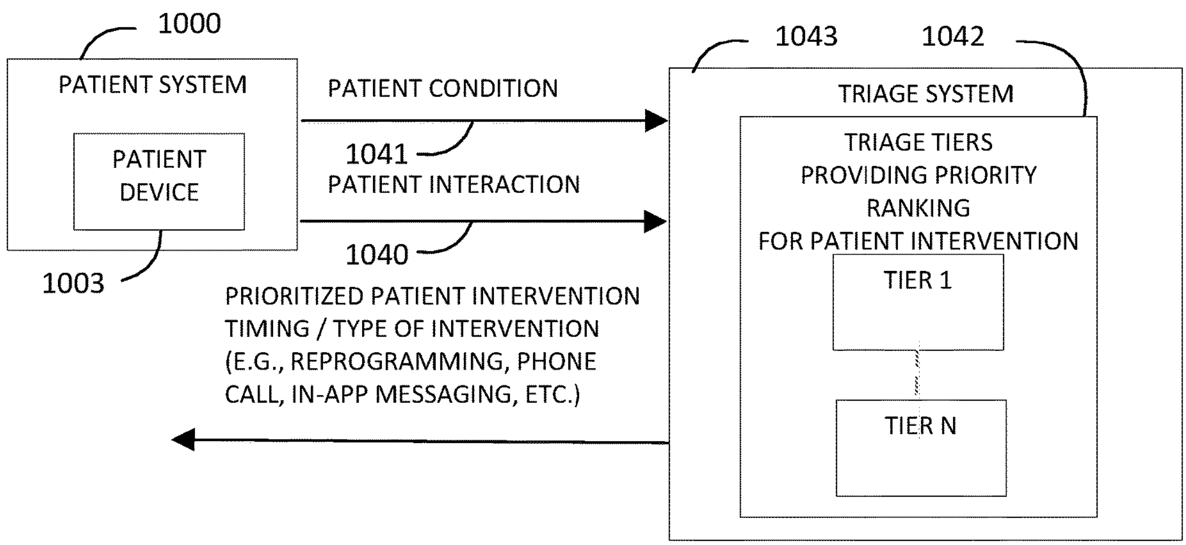
FIG. 10 illustrates, by way of example and not limitation, a system for triaging patients.

FIG. 10 illustrates, by way of example and not limitation, a system for triaging patients. The illustrated medical system may include a patient system 1000 configured to determine a condition of a patient and deliver a neuromodulation therapy. The patient system 1000 may include a patient device 1003, where the patient device has a user interface configured to enable patient interaction by the patient with the patient system. The triage system 1043 may be configured to select a triage tier 1042 from two or more triage tiers available for selection and indicative of a priority ranking for patient intervention. The triage system may include at least one processor configured to operate on instructions to receive the patient interaction 1040 and patient condition 1041 inputs and determine a triage tier based on the received patient condition and patient interaction inputs. The triage system 1043 may be configured to use both the interaction 1040 and the patient condition 1041 to select the triage tier. The triage tier may determine the timing (e.g., order) for intervening with patient and/or may determine type of patient intervention (e.g., reprogramming, phone call, text, email, in-app messaging, clinical appointments, automated or person-to-person message, and the like).

Figure 11:
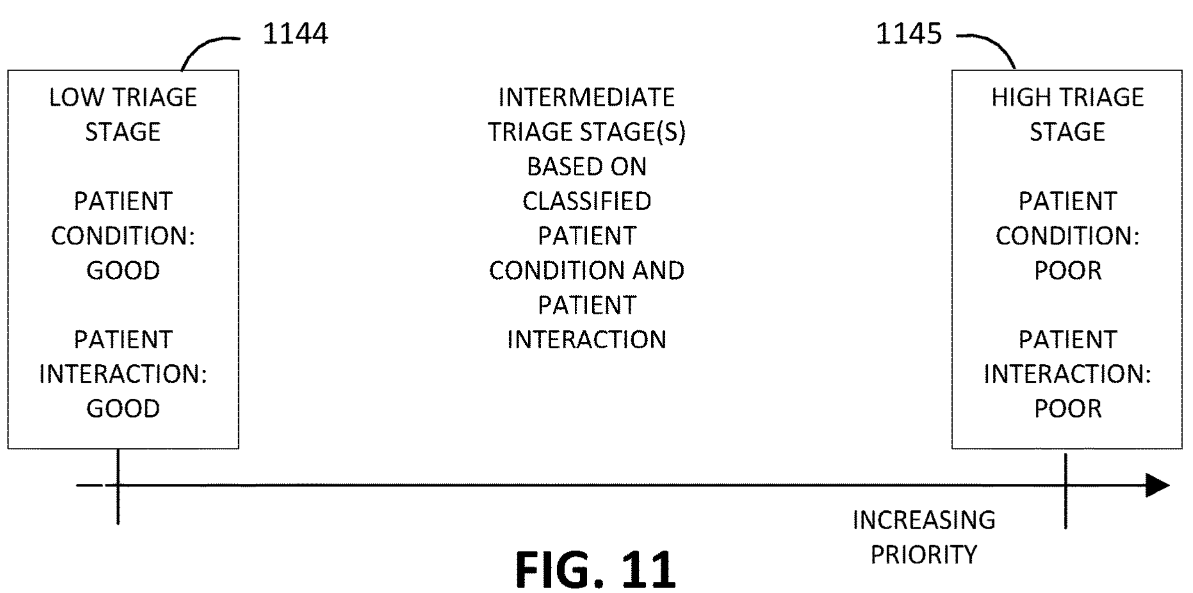
FIG. 11 illustrates, by way of example and not limitation, triage stages based on classified patient condition and a classified patient interaction.

FIG. 11 illustrates, by way of example and not limitation, triage stages based on classified patient condition and a classified patient interaction. The illustration shows a lower triage stage that has a low priority 1144 for patient invention, and a high triage stage 1145 that has a high priority for patient intervention. The low triage stage 1144 may be used when both the patient condition and the patient interaction are classified as good, and the high triage stage 1145 may be used when both the patient condition and the patient interaction are classified as poor. Additional, intermediate triage stages may be determined for other classifications of patient condition and patient interaction.

It is noted that additional criteria may be considered and classified to prioritize the patient into one of these tiers. For example, external topics that could be affecting pain may be detected from free text or questionnaires. For example, mental/emotional life changes, such as death, new job, or move) may affect a patient's condition. Disease progression, acute injury or mechanical pain, other health issues such as a co-morbidity, medication changes, and activity changes may also affect a patient's condition and satisfaction with the therapy. If the patient is experiencing other reasons that may be causing the patient's pain state, then the patient may be annotated with a corresponding symbol in the dashboard/portal. Additional information regarding these other reasons may be provided to the user upon selecting the patient or symbol.

Figure 12:
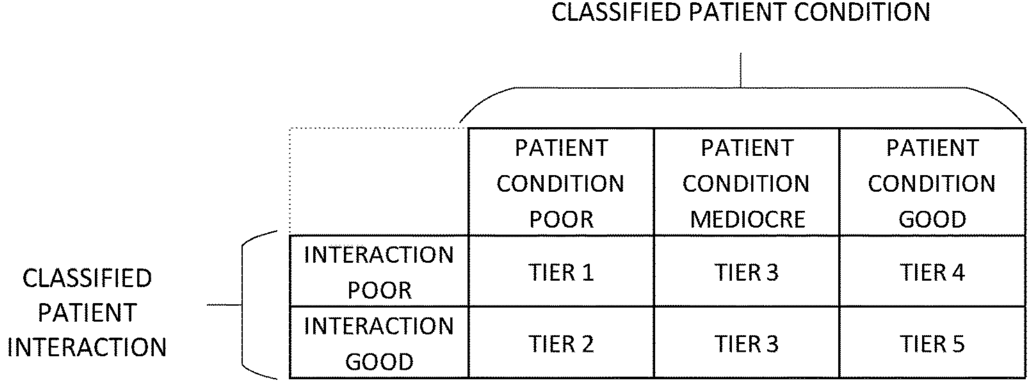
FIG. 12 illustrates, by way of example and not limitation, triage stages for two patient interaction classifications and three patient condition classifications.

FIG. 12 illustrates, by way of example and not limitation, triage stages for two patient interaction classifications and three patient condition classifications. As illustrated, the classifications for the patient interaction and patient condition may be used to select one of five tiers, as discussed below. By way of example and not limitation, some embodiments may classify patient condition into three classification levels (Good, Mediocre, Poor), and may classify patient interaction into two classification levels (Good, Poor). These classifications may be used to triage the patient into multiple tiers. The tiers of patients may be used to sort patients, tag those patients whose devices should be reprogrammed, determine those patients who need a phone call as they will not be monitoring their device, or determine those patients and situations that may benefit from an in-app message, text, email or other more passive communication. By way of example and not limitation, some embodiments may sort patients into one of the following five tiers.

Tier 1 may be used to identify the patients who are not doing well and are not using stimulator (off) or recent programs, and are thus are determined to be in need of the quickest intervention. The patient condition may be determined using any one or any combination of two or more of the following inputs. A pain state may be used. An input may include a satisfaction score, where a low score indicates that the patient condition is poor. For example, a patient may be asked, such as using a patient device such as a remote control or smart phone, how satisfied they are with their therapy or their experiences with the system. The use of the patient device may be preferred as allows for quicker analysis and intervention when needed. However, a clinician or device rep may ask the patient, or the patient may fill out a questionnaire in clinic or a home. The patient monitor system may provide other input from which it can be determined that the patient is not doing well. For example, the patient may provide a low satisfaction score. Other inputs may include a high pain score (which may be specific to an area), sleep (e.g., a low score for a length of time greater than a threshold, mood (low score), low effective mobility, low mobility minutes and low steps, free text (negative sentiment, keywords), pain states (long dwell time in low state), whether they would recommend the system to another person, use of communication channels with the clinician or device rep (multiple uses) such as in-app communication, text, or phone (determined through phone records, data sharing on phone, or reported by the device rep), remote control rating logs, activity (low) such as an activities of daily living (ADL) list, or various combinations thereof. An ADL list, for example, may include selections or other input that identify what activities the patients performed during the day. Such ADL items in the list may include sitting, standing, dressing, eating, bathing housework, driving, cooking, walking and/or running. A measure of low activity may be a low could of ADL items for the day. Some of these items may be weighted more than others, such that the lack of sitting or standing may strongly indicate low activity. Other inputs may include other biomarkers or sensors that may be indicative of pain, such as a high heart rate, body temperature, blood pressure, restless movements, galvanic skin response (GSR) sensors, facial sensors, low heart rate variability, and the like. Smartwatches or other personal devices may have their own metrics that are similar to low heart rate variability such as stress and body battery. There may be various ways to determine or estimate heart rate variability from inter-beat intervals. or other parameters There are also a number of inputs that can be used to determine a level of patient engagement with the system, including whether the patient uploaded medical device data, medical device usage (e.g., percentage ON/OFF, or time since ON), program usage (use of single or multiple neuromodulation programs, recency of creation of used programs, or time in each program), or changes in an amplitude of a program. Other inputs for determining patient engagement may include charging behavior (frequency, efficiency), remote control rating logs, or schedule usage. Furthermore, as a patient remote may include a button that can be used to turn off stimulation without unlocking the remote control, some embodiments may use the number or frequency of remote control unlocks for creating a connection between the medical device (e.g., implantable neuromodulator) and the remote control. Compliance voltage may be used as an input (e.g., compliance voltage at its max).

Tier 2 may identify patients that have low satisfaction and not doing well, but they are using stimulator (on) and/or their recent programs. For example, the patient may only be using one program or may be using multiple programs. The patient may be a good candidate for reprogramming.

Tier 3 may be for patients whose condition is mediocre. The patient may only be using one program, or may be using multiple programs. Examples of situations where the patient condition may be determined to be mediocre include situations where the patient's pain score is high but the patient has good sleep and activity. A patient's condition may be mediocre if it is neither "good" nor "poor", such as a patient who shows up to scheduled physician visit and say they are doing okay. Tier 3 recognizes that there may be a middling pain state as they are not yet at their goal for the therapy, but there may still be room for improvement as the patient is not engaged with the system. Tier 4 may be for patients that are doing well (good patient condition) but do not know how to use the device (low patient interaction); and Tier 5 may be for patients that are doing well (good patient condition), and that know now to use the neuromodulation system (good patient interaction).

Figure 13:
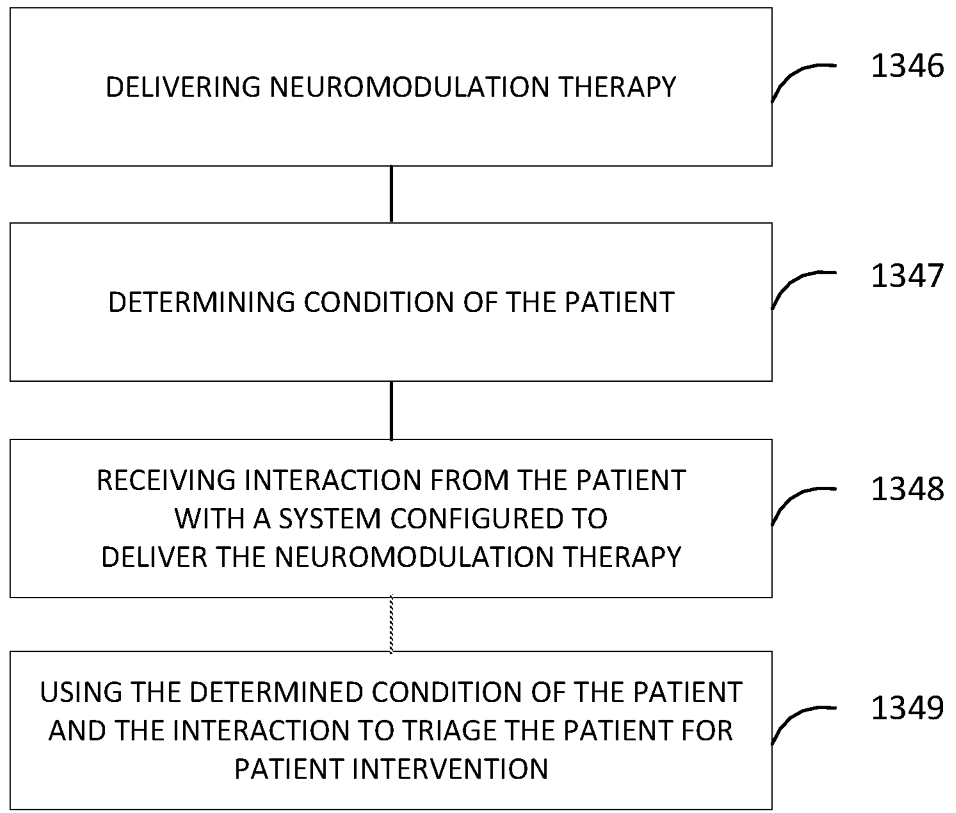
FIG. 13 illustrates, by way of example and not limitation, a method for triaging a patient, who is receiving neuromodulation therapy, for patient intervention.

FIG. 13 illustrates, by way of example and not limitation, a method for triaging a patient, who is receiving neuromodulation therapy, for patient intervention. The method may include delivering a therapy 1346 (e.g., a neuromodulation therapy such as an SCS or DBS therapy) and may include determining a condition of the patient 1347. A patient system (e.g., neuromodulation system and patient monitor system) may be used to deliver the therapy and determine the patient condition. The illustrated method further includes receiving interaction from the patient 1348 with the system that is configured to deliver the therapy. Both the patient interaction and the patient condition may be used to triage the patient for patient invention 1349.

Various embodiments may track activity in a web portal used by clinician or device reps to access patient information. A machine learning model to process the patient data to identify the patients most likely to get clicked on based on all patient data we have. For example, past "clicks" on patients may be evaluated in view of past patient data to determine when current patient data indicates that the patient may find intervention to be desirable. The user-selection, or "clicks", on the patient in the web portal may be separated by different categories of intervening people, such as device company's representative (device rep), device company's patient care team, or clinician. This information may be combined with data on the patients who more most likely to have their issues resolved with intervention to determine the triage level. The system may also determine a method of resolution that may be most appropriate or preferred specifically for the patient and the patient data for that patient (e.g., reprogramming, a phone call, a text, an email, in-app messaging, and the like).

Automatically Providing Patient Assistance

Various embodiments use patient monitoring to automatically provide assistance to the patient to improve their experience with the patient system, which may include improving the efficacy of the therapy. The patient monitoring system may collect a lot of patient data, such as watch, IPG, questionnaire, etc. Various embodiments leverage these data streams to appropriately assist the patient, such as but not limited to sending educational materials, making recommendations, and alerting clinician/rep that the patient needs help. Various algorithm modules may be deployed through the remote patient monitoring platform.

By way of example and not limitation, the system may be configured to automatically detect battery-related issues, such as trouble with the battery itself or with how the patient is charging the battery, from the monitored patient data. The system may be sensitive to both technical problems and user interaction problems. The system may further be configured to automatically send educational material (e.g., training video for recharging the device or other educational material) to the patient device when it automatically detects issues with the battery. For example, the system may detect battery issues when there is a consistently low battery voltage, when the charging rates for charging the batter are slow, when there are high temperatures (e.g., thermistor values) during charging, when there is an insufficient maximum voltage on the battery, when the therapy-delivering device (e.g., neuromodulator) is OFF more than expected, when the hibernation state frequency and duration are different than expected, when the charge current is low (e.g., below 25 mA), or when the frequency and efficiency of charging changes. The system may also detect battery issues from questionnaires or patient free text entries using topic modeling.

By way of another example and not limitation, the system may be configured to automatically detect patient issues with changing programs or program settings. The system may further be configured to automatically send educational material (e.g., training video for changing remote control settings or other educational material for changing programs or program settings) to the patient device when it automatically detects issues with changing programs or program settings. For example, the system may detect issues with changing programs or programming settings by detecting that program or program settings do not change and pain outcomes are not good, the therapy-delivering device (e.g., neuromodulator) is OFF more than expected (e.g., percentage OFF/ON or time since device is ON) and/or by monitoring program usage (e.g., single program vs multiple programs, recency of creation of programs implemented by the therapy-delivery device, and/or time in each program). The system may also detect issues with changing programs or program settings from questionnaires or patient free text entries using topic modeling.

By way of another example and not limitation, the system may be configured to automatically detect patient issues with creating, changing, starting and/or stopping therapy-delivery schedules. The system may further be configured to automatically send educational material (e.g., training video or other educational material for creating, changing, starting and/or stopping schedules) to the patient device when it automatically detects issues with creating, changing, starting and/or stopping schedules. The system may detect these issues by determining that a schedule on the therapy-delivery device was recently added but is not used and the patient condition (e.g., pain outcomes) are poor. The system may also detect issues with using therapy schedules from questionnaires or patient free text entries using topic modeling.

By way of another example and not limitation, the system may be configured to automatically detect patient issues with charging and/or using the patient device (e.g., remote control). The system may further be configured to automatically send educational material (e.g., training video or other educational material) to the patient device for charging and/or using the patient device when it automatically detects issues with charging and/or using the patient device. The system may detect these issues by determining that the patient never changes anything using the patient device, and the patient condition (e.g., pain outcomes) are poor. A user interface for a patient device may be normally "locked" and may be "unlocked" by the patient (via a passcode, biometrics, and the like) to allow the patient to interact with the programming of the device. The system may determine that the patient infrequency unlocks the remote control (connection between IPG and RC; compliance voltage is at its max; battery levels). For example, a remote control may include a button that can be used to quickly turn off the therapy without having to unlock a user interface of the remote control. Some embodiments may monitor for the use of this button. The system may also detect issues with charging and/or using the device from questionnaires or patient free text entries using topic modeling.

By way of another example and not limitation, the system may be configured to automatically detect patient issues with uploading the therapy-delivering device data (e.g., implantable medical device "IMD" data. The system may further be configured to automatically send educational material (e.g., training video or other educational material for charging and/or using the patient device) to the patient device when it automatically detects issues with uploading the therapy-delivering device data. The system may detect these issues by determining that no uploaded data exists in the system or app logs show failed data upload attempts. The system may also detect issues with uploading data from questionnaires or patient free text entries using topic modeling.

By way of another example and not limitation, the system may be configured to automatically detect patient issues with connecting and/or recharging a wearable patient device such as a watch. The system may further be configured to automatically send educational material (e.g., training video or other educational material for connecting and/or recharging the watch) to the patient device when it automatically detects issues with connecting and/or recharging the watch. The system may detect these issues by determining that there is no uploaded watch data or watch battery levels are consistently low (lower than a threshold) for periods of time longer than a threshold. The system may also detect issues with connecting and/or recharging a watch or other wearable patient device from questionnaires or patient free text entries using topic modeling.

The system may be configured to automatically detect patient issues for which the patient may benefit from recommendations (e.g., troubleshooting), and then automatically send the recommendations when the issue is automatically detected; and/or may be configured to automatically detect patient issues for which the patient may benefit from reprogramming, and then automatically alert the clinician or device rep when the issue is automatically detected. The system may detect these issues with from questionnaires or patient free text entries using topic modeling. In a system configured to deliver neuromodulation therapy to treat pain, for example, the system may monitor free text for words such as "new pain", "not covering pain area", "cannot feel stimulation" when the program is intended to cause paresthesia, "stimulation is too strong", "stimulation is felt in unwanted areas which are not painful", and the like. The system may further be configured to automatically send a campaign to have the patient measure overlap between stimulation and pain area, and if it is determined that that the stimulation and pain area do not sufficiently overlap, then suggest program changes; and/or the system may further be configured to alert the clinician/device rep that the patient needs reprogramming. The system may further be configured to automatically send a campaign to have patient measure impedances on device, and if it is determined that any impedances are off (e.g., too high), alert clinician/rep that patient needs reprogramming.

The system may further be configured to automatically determine when the patient is indicating that stimulation is not felt, and respond by sending a recommendation to the patient to increase the amplitude of the electrical therapy (e.g., neuromodulation). The system may monitor, after the amplitude increase, whether the patient continues to indicate that stimulation is not felt and then suggest that the patient contact the device rep and/or alert the clinician that the patient's therapy-delivering device should be reprogrammed.

The system may further be configured to automatically determine when the patient is indicating that stimulation is too strong, and respond by sending a recommendation to the patient to decrease the amplitude of the electrical therapy (e.g., neuromodulation). The system may monitor, after the amplitude increase, whether the patient continues to indicate that stimulation is too strong, and then suggest that the patient contact the device rep and/or alert the clinician that the patient's therapy-delivering device should be reprogrammed.

The system may further be configured to automatically detect issues other than the delivered therapy that could be affecting pain. For example, the system may detect these issues from questionnaires or patient free text entries using topic modeling. Examples of such issues may include, but are not limited to: mental or emotional life changes such as a death, new job, move, and the like; disease progression; acute injury or mechanical pain; co-morbidities or other health issue(s); medication changes; and activity changes which may be detectable from activity questions and/or wearable data. The patient's name or other identifier may be annotated with a symbol in a dashboard/portal when it is determined that some other factor may be influencing their pain state. Additional information may be provided when the symbol or patient's name or another identifier is clicked. The system may be configured to automatically send a reminder to the device rep and/or clinician to check in on the patient, with or without a time interval to wait before interacting with the patient (e.g., such as may be appropriate to allow a bereavement period of time if the patient is mourning a death).

The system may be configured to monitor patient data, such as free text or questionnaires, to identify candidates for clinical trial enrollment. For example, a patient may write in free text that they have pain in an area, and the system determines that area is an area that may be tested for a new indication or another disease state that could be treated with SCS. Conversely, the system may be configured to monitor patient data, such as free text or questionnaires, to exclude the patient from being enrolled in a potential study. For example, a patient may be excluded if it is determined that the patient is not compliant with the prescribed therapy, does not keep the therapy-delivery device charge, or does not fill out surveys.

A benefit for automatically sending assistance to the patient is that a number of problematic issues may be satisfactorily addressed without involving reps, which will free up their time elsewhere. Also, automatically sending assistance may quickly improve common patient issues, which may increase patient satisfaction with the system.

Figure 14:
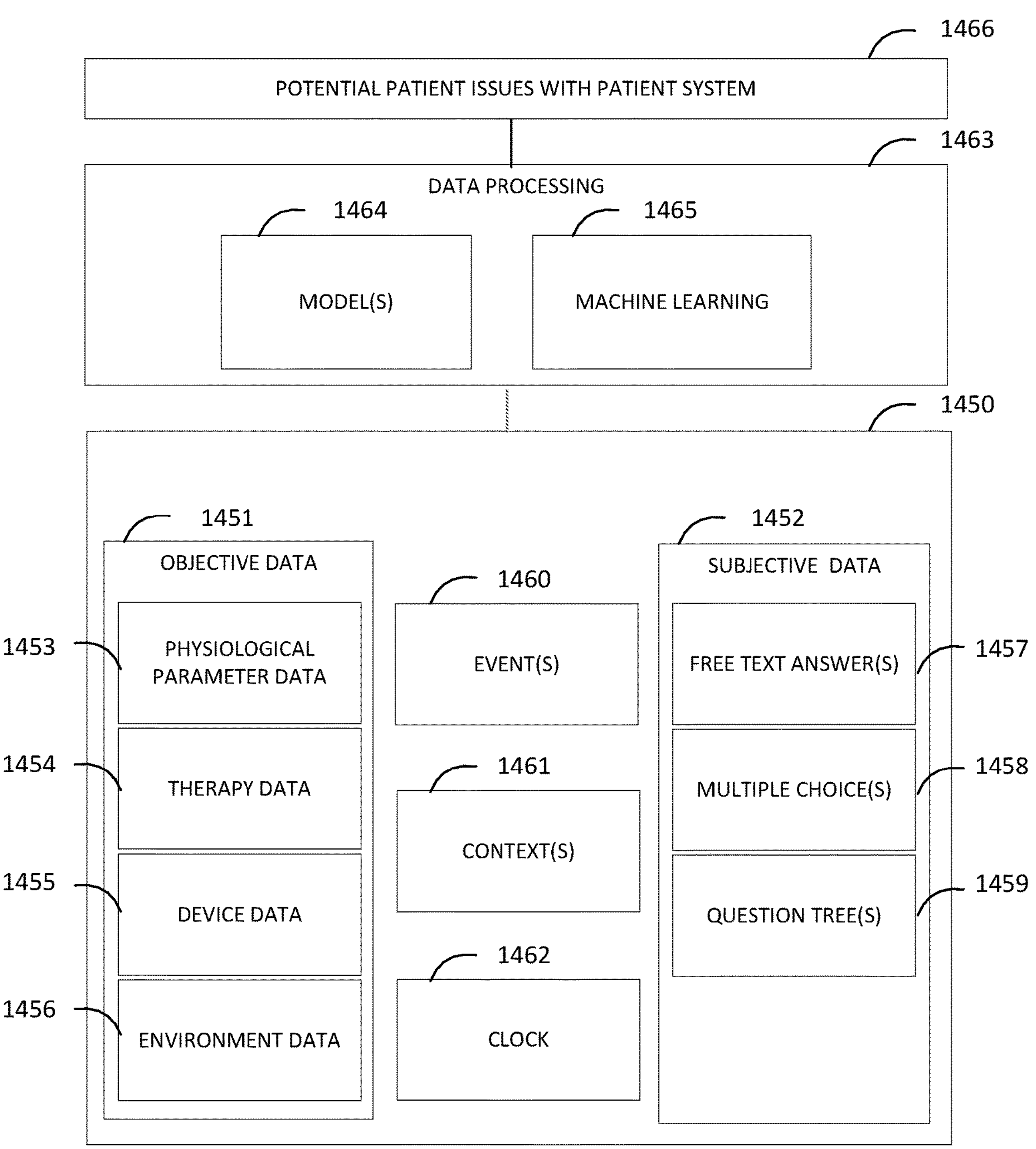
FIG. 14 illustrates, by way of example and not limitation, a satisfaction monitor configured to determine, from the health-related information, that patient issue(s) may be adversely affecting the patient satisfaction with the patient system.

FIG. 14 illustrates, by way of example and not limitation, a satisfaction monitor configured to determine, from the health-related information, that patient issue(s) may be adversely affecting the patient satisfaction with the patient system. The satisfaction monitor may collect different healthcare-related data types 1450 which may include objective data 1451 and/or subjective data 1452. Objective data is data that can be observed using our senses, and may be obtained from a measurement or direct observation. Objective data may be measured by a sensor and may be provided via user input when the user has access to objectively determined information. Examples of objective data may include physiological parameter data 1453, therapy data 1454, device data 1455, and environmental data 1456. By way of example and not limitation, physical parameter data 1453 may include data such as: heart rate, blood pressure, respiration rate, activity, posture, electromyograms (EMGs), neural responses such as evoked compound action potentials (ecaps), glucose measurements, oxygen levels body temperature, oxygen saturation and gait. By way of example and not limitation, therapy data 1454 may include: neuromodulation programs, therapy on/off schedule, dosing, neuromodulation parameters such as waveform, frequency, amplitude, pulse width, period, therapy usage and therapy type. By way of example and not limitation, device data 1455 may include: battery information (voltage, charge state, charging history if rechargeable), impedance data, faults, device model, lead models, MRI status, Bluetooth connection logs, connection history with Clinician's Programmer (CP). By way of example and not limitation, environmental data 1456 may include: temperature, air quality, pressure, location, altitude, sunny, cloudy, precipitation, etc. Subjective data may include information received from the patient. For example, the patient's quantification of pain is a subjective data. Subjective data may generally involve user-inputted data. Examples of subjective data 1452 include questions with free text answers 1457, multiple choice questions 1458, and question tree(s) 1459. Other data may be stored and/or transferred, including detected event(s) 1460, contextual data 1461 for other collected data and/or event(s), and a clock/time 1462 such as may be used to provide a time stamp associated with the retrieved data. The event(s), context(s) and time may be detected by the system or may be provided via user input.

The collected data may be processed, as generally illustrated at 1463. The data processing may occur in a medical device or a patient device such as a phone, tablet, or remote control, or may occur in a remote data receiving system. The data processing may include one or more model(s) 1464. These model(s) may be used to determine how the patient data is used to determine issues (e.g., "common issues") for which automatic patient assistance may be beneficial 1466. These model(s) also may be used to determine how the patient data is used to classify the patient condition (such as disease progression or state) or the patient interaction, determine the type and contact of intervention, determine issues (e.g., "common issues") for which automatic patient assistance may be beneficial, and determine content for the patient assistance. These model(s) may use the acquired data to deliver therapy. Machine learning 1465 may be implemented on the collected data to develop or refine the model(s) 1464. The data processing may include data imputation, which refers to a process of replacing missing data with substituted values such as may be used to prevent missing data from introducing bias into the model(s) or machine learning.

Figure 15:
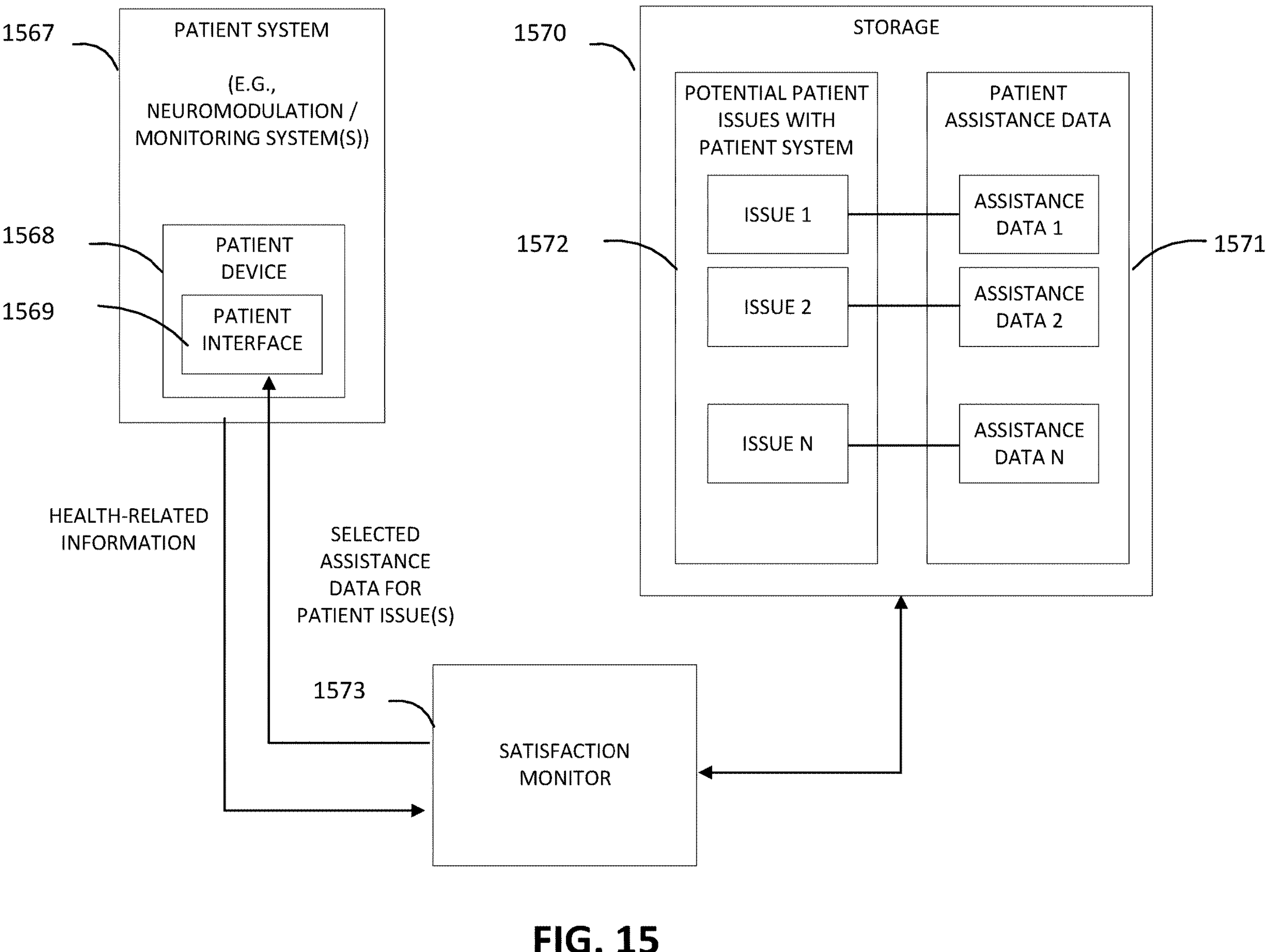
FIG. 15 illustrates, by way of example and not limitation, a system for using a satisfaction monitor to determine that patient issue(s) and provide patient assistance data for the patient issues.

FIG. 15 illustrates, by way of example and not limitation, a system for using a satisfaction monitor to determine that patient issue(s) and provide patient assistance data for the patient issues. The system may be configured for use to determine health-related information for a patient, and deliver a neuromodulation therapy. The system may include a patient system 1567, which may include a neuromodulation system and patient monitoring system. The patient system 1567 may include a patient device 1568 (e.g., remote control, phone, tablet, etc.) having a user interface 1569. The system may include storage 1570 for storing patient assistance data 1571 for each of a plurality of issues 1572 that may adversely affect patient satisfaction with the patient system. The system may include a satisfaction monitor 1573 configured to determine, from the health-related information, that at least one of the plurality of issues may be adversely affecting the patient satisfaction; and send the patient assistance data, that corresponds to the at least one of the plurality of issues, to the user interface.

Figure 16:
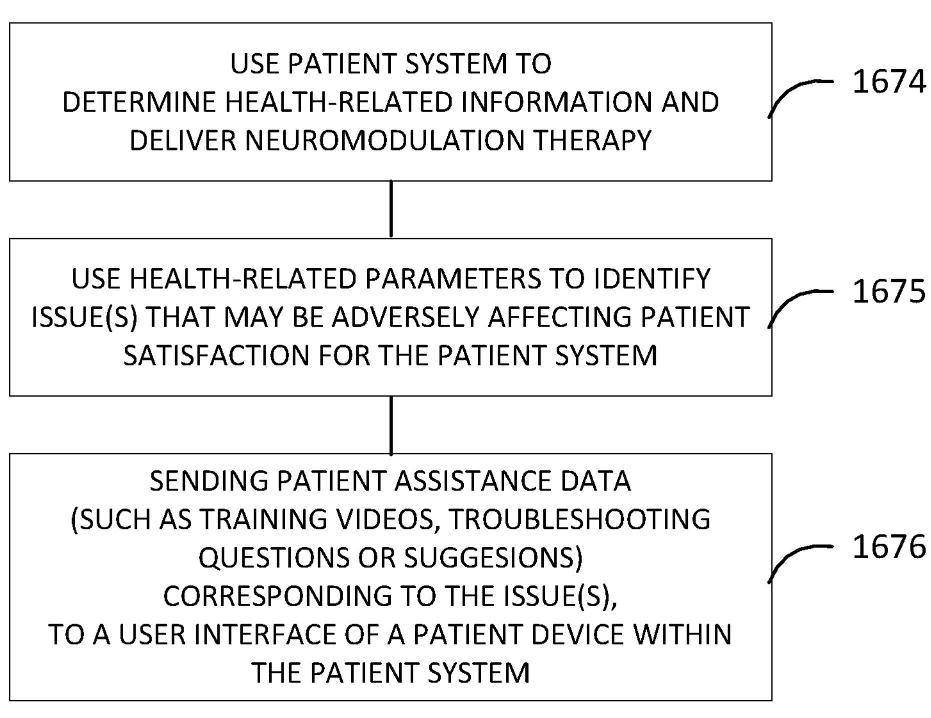
FIG. 16 illustrates, by way of example and not limitation, a method for identifying patient issues, and sending patient assistance data.

FIG. 16 illustrates, by way of example and not limitation, a method for identifying patient issues, and sending patient assistance data. The method may be performed using a medical system that includes a patient system configured to determine health-related information for a patient and deliver a neuromodulation therapy. The method may include using the patient system to determine health-related information for a patient and deliver neuromodulation therapy to the patient 1674. The method may include identifying, from the health-related information, at least one of a plurality of issues that may be adversely affecting patient satisfaction for the patient system, wherein the plurality of issues corresponds to stored patient assistance data 1675. The method may further include sending the patient assistance data, that corresponds to the at least one of the plurality of issues, to a user interface of a patient device within the patient system 1676.

Figure 17:
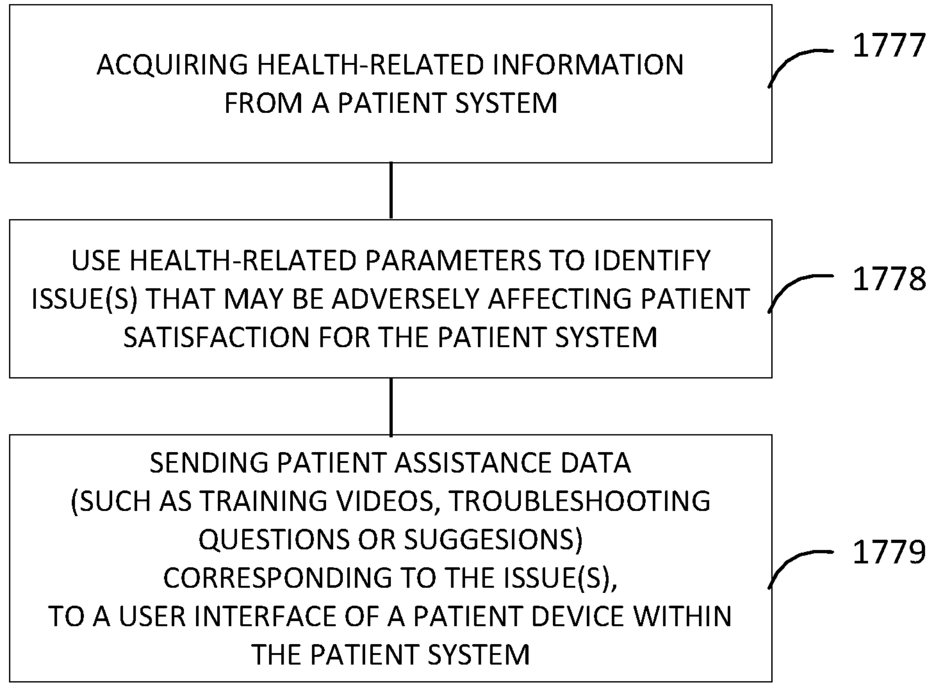
FIG. 17 illustrates, by way of example and not limitation, a method performed by a satisfaction monitor to send patient assistance data corresponding to patient issue(s).

FIG. 17 illustrates, by way of example and not limitation, a method performed by a satisfaction monitor to send patient assistance data corresponding to patient issue(s). The method may be performed by implementing instructions (e.g., software and/firmware) stored in a non-transitory machine-readable medium. The method may include acquiring health-related information from a patient system that is configured to determine the health-related information for a patient and deliver a neurostimulation therapy 1777. The method may further include identifying, from the health-related information, at least one of a plurality of issues may be adversely affecting the patient satisfaction with the patient system, wherein the plurality of issues corresponds to stored patient assistance data 1778. The method may further include sending the patient assistance data, that corresponds to the at least one of the plurality of issues, to a user interface of the patient system 1779.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks or cassettes, removable optical disks (e.g., compact disks and digital video disks), memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method, comprising:

delivering a neuromodulation therapy to a patient to treat a condition of the patient using a neuromodulation system, the neuromodulation system including a therapy-delivering device and a patient device having a user interface configured to enable patient interaction with the neuromodulation system;

determining the condition of the patient by using the neuromodulation system to analyze healthcare-related data, the healthcare-related data including at least one of patient-reported data or sensor-based data, the patient-reported data being derived from patient inputs on the user interface of the patient device, and the sensor-based data including at least one patient parameter sensed by a sensor of the neuromodulation system;

determining, using the neuromodulation system, patient interaction data, the patient interaction data being indicative of patient engagement with the neuromodulation system via the user interface of the patient device, the patient interaction data including at least one of: usage of the patient device to change a parameter of the neuromodulation therapy, usage of the patient device to change programs used to deliver the neuromodulation therapy, or usage of the patient device to turn the neuromodulation therapy ON or OFF;

using both the determined condition of the patient and the determined patient interaction data jointly to triage the patient into one of a set of two or more triage tiers indicative of a priority ranking for patient intervention, wherein the triage tier is determined based on a combination of the determined condition and the determined patient interaction data such that neither the determined condition alone nor the determined patient interaction data alone determines the triage tier; and automatically assisting the patient based on the triage tier by accessing a data store storing patient assistance data corresponding to each of a plurality of stored patient issues associated with operation of the neuromodulation system, automatically identifying, from the plurality of stored patient issues, at least one issue adversely affecting patient satisfaction with the neuromodulation system based on the determined patient interaction data and the determined condition of the patient, and automatically transmitting therapy adjustments to the therapy-delivering device based on the identified issue and the triage tier.

2. The method of claim 1, further comprising using a patient monitoring system configured to determine the condition of the patient.

3. The method of claim 1, further comprising using a remote system to provide the patient intervention to improve the condition of the patient, wherein the patient intervention includes at least one of reprogramming, a phone call, or an in-app patient message.

4. The method of claim 1, further comprising using a classification of the condition of the patient and a classification of the patient interaction to select the triage tier.

5. The method of claim 4, wherein:

the classification of the condition includes a good condition and a poor condition;

the classification of the patient interaction includes a good interaction and a poor interaction; and the two or more triage tiers available for selection include at least four tiers, including:

a first tier corresponding to the poor condition and the poor patient interaction;

a second tier corresponding to the poor condition and the good patient interaction;

a third tier corresponding to the good condition and the poor interaction; and a fourth tier corresponding to the good condition and the good patient interaction.

6. The method of claim 5, wherein the classification of the condition includes a mediocre condition between the good condition and the poor condition, and the at least four tiers include a tier corresponding to the mediocre condition and the good patient interaction.

7. The method of claim 1, wherein the patient condition is determined by receiving the patient inputs on the user interface, the patient inputs including, for the patient, at least one of a pain state, a satisfaction score, a pain score, or duration in pain state.

8. The method of claim 1, wherein the patient condition is determined by receiving the patient inputs on the user interface, the patient inputs including, for the patient, at least one of a sleep score, a mood score, or an activity score.

9. The method of claim 1, wherein the patient condition is determined using the sensor-based data by receiving, for the patient, sensed patient parameters, and determining the patient condition from the sensed patient parameters.

10. The method of claim 1, wherein the patient condition is determined by receiving the patient inputs on the user interface, the patient inputs including, for the patient, free text, and determining the patient condition from the free text.

11. The method of claim 1, wherein the patient condition is determined by receiving the patient inputs on the user interface, the patient inputs including, for the patient, a remote control rating log, whether the patient would recommend the neuromodulation therapy to another person, or the use of a communication channel with medical device reps.

12. The method of claim 1, further comprising determining the patient condition by tracking web portal activity for patients by a clinician or a rep, or determining factors other than the neuromodulation therapy that may be influencing a pain state.

13. The method of claim 1, further comprising determining the patient interaction by determining how often the patient changes a parameter of the neuromodulation therapy.

14. The method of claim 1, further comprising determining the patient interaction by determining how often the patient changes programs used to deliver the neuromodulation therapy.

15. The method of claim 1, further comprising determining the patient interaction by determining how long the patient has left the neuromodulation therapy OFF or how long the patient has left the neuromodulation therapy ON.

16. A non-transitory machine-readable medium including instructions, which when executed by a machine, cause the machine to perform a method comprising:

delivering a neuromodulation therapy to a patient to treat a condition of the patient using a neuromodulation system, the neuromodulation system including a therapy-delivering device and a patient device having a user interface configured to enable patient interaction with the neuromodulation system;

determining the condition of the patient by using the neuromodulation system to analyze healthcare-related data, the healthcare-related data including at least one of patient-reported data or sensor-based data, the patient-reported data being derived from patient inputs on the user interface of the patient device, and the sensor-based data including at least one patient parameter sensed by a sensor of the neuromodulation system;

determining, using the neuromodulation system, patient interaction data, the patient interaction data being indicative of patient engagement with the neuromodulation system via the user interface of the patient device, the patient interaction data including at least one of: usage of the patient device to change a parameter of the neuromodulation therapy, usage of the patient device to change programs used to deliver the neuromodulation therapy, or usage of the patient device to turn the neuromodulation therapy ON or OFF;

using both the determined condition of the patient and the determined patient interaction data jointly to triage the patient into one of a set of two or more triage tiers indicative of a priority ranking for patient intervention, wherein the triage tier is determined based on a combination of the determined condition and the determined patient interaction data such that neither the determined condition alone nor the determined patient interaction data alone determines the triage tier; and automatically assisting the patient based on the triage tier by accessing a data store storing patient assistance data corresponding to each of a plurality of stored patient issues associated with operation of the neuromodulation system, automatically identifying, from the plurality of stored patient issues, at least one issue adversely affecting patient satisfaction with the neuromodulation system based on the determined patient interaction data and the determined condition of the patient, and automatically transmitting therapy adjustments to the therapy-delivering device based on the identified issue and the triage tier.

17. A medical system, comprising:

a neuromodulation system including a patient device configured to determine a condition of a patient and a therapy-delivering device configured to deliver a neuromodulation therapy, wherein the patient device has a user interface configured to enable patient interaction by the patient with the neuromodulation system, wherein the condition of the patient is determined by analyzing healthcare-related data, the healthcare-related data including at least one of patient-reported data or sensor-based data, the patient-reported data being derived from patient inputs on the user interface of the patient device, and the sensor-based data including at least one patient parameter sensed by a sensor of the neuromodulation system, the neuromodulation system being configured to determine patient interaction data indicative of patient engagement with the neuromodulation system via the user interface of the patient device, the patient interaction data including at least one of: usage of the patient device to change a parameter of the neuromodulation therapy, usage of the patient device to change programs used to deliver the neuromodulation therapy, or usage of the patient device to turn the neuromodulation therapy ON or OFF; and a triage system configured to select a triage tier from two or more triage tiers available for selection and indicative of a priority ranking for patient intervention, wherein the triage system is configured to use both the determined patient interaction data and the determined condition jointly to select the triage tier, wherein the triage tier is determined based on a combination of the determined condition and the determined patient interaction data such that neither the determined condition alone nor the determined patient interaction data alone determines the triage tier, wherein the triage system is configured to access a data store storing patient assistance data corresponding to each of a plurality of stored patient issues associated with operation of the neuromodulation system, automatically identify, from the plurality of stored patient issues, at least one issue adversely affecting patient satisfaction with the neuromodulation system based on the determined patient interaction data and the determined condition of the patient, and automatically transmit therapy adjustments to the therapy-delivering device based on the identified issue and the triage tier.

18. The medical system according to claim 17, wherein the neuromodulation system includes a patient monitoring system configured to determine the condition of the patient.

19. The medical system according to claim 17, wherein the triage system includes a remote system configured for use in providing the patient intervention to improve the condition of the patient, wherein the patient intervention includes at least one of reprogramming, a phone call, or an in-app patient message.

20. The medical system according to claim 17, wherein the triage system is configured to use a classification of the condition of the patient and a classification of the patient interaction to select the triage tier.

* * * * *